United States Patent [19]

Pelletier

[11] Patent Number: 5,716,956
[45] Date of Patent: Feb. 10, 1998

[54] DIHYDROPHTHALAZINE ANTAGONISTS OF EXCITATORY AMINO ACID RECEPTORS

[75] Inventor: Jeffrey C. Pelletier, Lafayette Hill, Pa.

[73] Assignee: Bearsden Bearsden Bio, Inc., Philadelphia, Pa.

[21] Appl. No.: 588,145

[22] Filed: Jan. 18, 1996

Related U.S. Application Data

[63] Continuation-in-part of Ser. No. 476,272, Jun. 7, 1995.
[51] Int. Cl.$^6$ .................................................. C07D 237/30
[52] U.S. Cl. ........................... 514/248; 544/234; 544/237
[58] Field of Search ................................. 544/237, 234; 514/248

[56] References Cited

U.S. PATENT DOCUMENTS

| | | | |
|---|---|---|---|
| 2,832,769 | 8/1958 | Armstrong | 544/237 |
| 3,012,033 | 12/1961 | Engelbrecht et al. | 544/237 |
| 3,022,305 | 2/1962 | Carboni | 544/237 |
| 3,249,611 | 5/1966 | Hirach et al. | 544/237 |
| 3,274,185 | 9/1966 | Sigal et al. | 544/237 |
| 3,753,988 | 8/1973 | Rodway et al. | 514/248 |
| 3,880,881 | 4/1975 | Singh . | |
| 4,963,676 | 10/1990 | Strekowski et al. | 544/237 |
| 5,089,494 | 2/1992 | Iwase et al. | 544/237 |
| 5,110,347 | 5/1992 | Selby | 544/234 |
| 5,643,911 | 7/1997 | Yamada et al. | 514/248 |

FOREIGN PATENT DOCUMENTS

| | | | |
|---|---|---|---|
| 0475527A2 | 3/1992 | European Pat. Off. . | |
| 03-55529 | 3/1991 | Japan | 544/237 |

OTHER PUBLICATIONS

Wilding T. Molecular Pharmacol. vol. 47 pp. 582–587 1995.
Donevan, S Jour. Pharmac. and Exptc Therap vol. 271 pp. 25–29 1994.
Zorumski, C. Neuron vol. 10 pp. 61–67 1993.
Chen et al., "Evaluation of Five Methods for Testing Anticonvulsant Activities," Proc. Sco. Exp. Biol. Med., 87:334 (1954).
Donevan and Rogawski, "GYKI 52466,aα2,3–Benzodiazepine, Is a Highly Selective, Noncompetitive Antagonist of AMPA/kainate Receptor Responses," Neuron, 10:51—59 (1993).
Hussy and et al., "Function Properties Of A Cloned 5–hydroxytryptamine Ionotropic Receptor Subunit :Comparison With Native Mouse Receptors," J. Physiol. (Lond.), 481.2:311–323 (1994).
Lipton and Rosenberg, "Excitatory Amino Acids As A Final Common Pathway For Neurologic Disorders," New England Journal of Medicine, 330:613–622 (1994).
McBurney, "Therapeutic Potential of NMDA Antagonists in Neurodegenerative Diseases," Neurobiology of Aging, 15:271–273 (1994).
Meldrum and Smith, "Cerebroprotective Effect of a Non–N–Methyl–D–Aspartate Antagonist, GYKI 52466, After Focal Ischemia in the Rat," Stroke 23:861 (1992).
Meldrum, "Excitatory Amino Acids in Epilepsy and Potential Novel Therapies," Epilepsy Research, 12:189–196 (1992).
Peillet et al., "The non–NMDA antagonists, NBOX and GYKI 52466, protect against cortical and striatal cell loss following transient global ischamia in he rat," Brain Res., 571:115 (1992).
Yamaguchi et al., "Anticonvulsant Activity of AMPA/kainate antagonists:Comparison of GYKI 52466 and NBOX in Maximal Electroshock and Chemoconvulsant Seizure Models," Epilepsy Research, 15:179–184 (1993).
Tarnawa et al., "Electrophysiological Studies With a 2,3–benzodiazepine Muscle Relaxant:GYKI 52466,"Eur. J. Pharmacol., 167:193–199 (1989).
Pelletier et al. Jour. Med. Chem vol. 39 No. 2 pp. 343–346 (Jan. 19, 1996).

Primary Examiner—Donald G. Daus
Attorney, Agent, or Firm—Arnall Golden & Gregory, LLP

[57] ABSTRACT

Substituted dihydrophthalazine compositions are provided which are active as non-NMDA ionotropic excitatory amino acid (EAA) receptor antagonists. The compositions are useful for treating disorders associated with excessive activation of the non-NMDA subtype of the ionotropic EAA receptor. The compounds further are useful as testing agents to identify and characterize other compounds for the treatment of these disorders. The compounds are useful therapeutically as sedatives or for the treatment of neuropsychopharmacological disorders such as stroke, ischemia and epilepsy. The compositions may be provided in combination with a suitable carrier for oral or parenteral administration. The compounds may be administered orally or parenterally for the treatment of a variety of disorders associated with non-NMDA EEA receptor function.

9 Claims, No Drawings

5,716,956

DIHYDROPHTHALAZINE ANTAGONISTS OF EXCITATORY AMINO ACID RECEPTORS

This application is a continuation-in-part of U.S. Ser. No. 08/476,272, filed Jun. 7, 1995, by Jeffrey C. Pelletier, the disclosure of which is incorporated herein by reference.

BACKGROUND OF THE INVENTION

This invention relates to dihydrophthalazine compounds useful as antagonists of excitatory amino acid receptors.

During the past fifteen years a great deal of attention has been directed toward the excitatory amino acids (EAA's), glutamate and aspartate, since they are believed to be the neurotransmitters responsible for the fast excitatory transmission in the mammalian central nervous system. The ionotropic EAA receptors are generally sub-classified into NMDA and non-NMDA receptors. These classifications are defined by those receptors which preferentially bind N-methyl-D-aspartate (NMDA) and those that are not responsive to NMDA but responsive to α-amino-3-hydroxy-5-methyl-4-isoxazoleproprionic acid (AMPA) or kainic acid (KA).

Tarnawa et al. describe 2,3-benzodiazepines (*Eur. J. Pharmacol.*, 167:193–199, 1989) which inhibit AMPA stimulated currents in neuronal cells. The 2,3-benzodiazepines such as GYKI 52466 and 53655 described by Tarnawa are non-competitive AMPA antagonists which bind to a novel modulatory site on the AMPA receptor. Meldrum (*Stroke*, 23:861, 1992 & *Brain Res.*, 571:115, 1992) has shown that GYKI 52466 is effective in rat models of both global and focal ischemia. GYKI 52466 was effective in a middle cerebral artery occlusion (MCAO) model of ischemia when given either continuously for 2 hours just after occlusion or delayed for one hour. The compounds reduced cortical infarct volumes by 68% and 48% respectively. In another model of neurodegenerative disease, GYKI 52466 was as effective as the glutamate site competitive antagonist NBQX in rat common carotid arteries model of global ischemia. These two animal models suggest that these compounds may be useful for the treatment of stroke and neurodegenerative ischmic conditions.

Efforts to find NMDA receptor antagonists and blockers which are neuroprotective have been very successful while efforts to find specific non-NMDA receptor antagonists have been much less successful. A number of pharmaceutical companies have pursued development of ion channel blockers or full antagonists of the NMDA receptor to protect against both chronic and acute neurodegenerative processes. Although some compounds have entered clinical trials, there has been only limited progress in developing a clinically useful NMDA receptor antagonist. Though non-NMDA antagonists have been shown to be useful in neuroprotective models in animals, there has been no progress in developing a clinically useful AMPA receptor antagonist.

It is an object of the invention to provide compounds which are useful as non-NMDA glutamate receptor antagonists as well as methods for their synthesis. It is a further object of the invention to provide non-NMDA receptor antagonists which are useful as sedatives or for the treatment of neuropsychopharmacological disorders such as stroke, ischemia and epilepsy. It is yet another object of the invention to provide compounds which are useful for the treatment of neurological, neuropsychiatric, neurogenerative and functional disorders associated with excessive activation of the non-NMDA subtypes of the ionotropic EAA receptor.

SUMMARY OF THE INVENTION

Compositions are provided which are active as non-NMDA ionotropic excitatory amino acid (EAA) receptor antagonists, in particular, which bind to the KA and/or AMPA receptors, and which therefore are useful for treating disorders associated with excessive activation of the non-NMDA subtypes of the ionotropic EAA receptors. The compounds further are useful as testing agents to identify and characterize other compounds for the treatment of these disorders.

Illustrative compounds include:

4-(4-Aminophenyl)-1,2-dihydro-1-methyl-2-ethylcarbamoyl-6,7-methylenedioxyphthalazine, 4-(4-Aminophenyl)-1,2-dihydro-1-methyl-2-propylcarbamoyl-6,7-methylenedioxyphthalazine, 4-(4-Aminophenyl)-1,2-dihydro-1-methyl-2-n-butylcarbamoyl-6,7-methylenedioxyphthalazine, 4-(3-Aminophenyl)-1,2-dihydro-1-methyl-2-n-butylcarbamoyl-6,7-methylenedioxyphthalazine, and 4-(4-Aminophenyl)-1,2-dihydro-1-methyl-2-propylthiocarbamoyl-6,7-methylenedioxyphthalazine.

The compositions may be provided in combination with a suitable carrier for oral or parenteral administration. The compounds may be administered orally or parenterally for the treatment of a variety of disorders associated with non-NMDA glutamate receptor function. The compositions may be used, for example, as sedatives or for the treatment of neuropsychopharmacological disorders such as stroke, ischemia and epilepsy.

DETAILED DESCRIPTION OF THE INVENTION

I. Glossary of Terms

The term "antagonist" as used herein means any compound which reduces the flow of cations through the non-NMDA receptor.

The term "neuropsychopharmacological disorder" as used herein means a disorder resulting from or associated with an excessive flux of ions through the AMPA receptor ligand-gated cation channels, and includes chemical toxicity (including substance tolerance and addiction), excitotoxicity, neurodegenerative disorders (such as Huntington's disease, Parkinson's disease, and Alzheimer's disease), post-stroke sequelae, epilepsy, seizures, mood disorders (such as bipolar disorder, dysthymia, and seasonal affective disorder), and depression. Neurodegenerative disorders can result from dysfunction or malfunction of the AMPA receptor.

The term "NMDA receptor" as used herein means a receptor which is stimulated, at a minimum, by the excitatory amino acids glutamic acid as well as by NMDA, but is not stimulated by AMPA or KA. It is a ligand-gated receptor.

The term "AMPA receptor" as used herein means a receptor which is stimulated, at a minimum, by the excitatory amino acids glutamic acid as well as by AMPA, but is not stimulated by NMDA. It is a ligand-gated receptor.

The term "Kainate receptor" as used herein means a receptor which is stimulated, at a minimum, by the excitatory amino acids glutamic acid as well as by KA, but is not stimulated by NMDA or AMPA. It is a ligand-gated receptor.

Pharmaceutically acceptable salts include both the metallic (inorganic) salts and organic salts; a list of which is given in Remington's Pharmaceutical Sciences 17th Edition, p. 1418 (1985). It is well known to one skilled in the art that an appropriate salt form is chosen based on physical and chemical stability, flowability, hygroscopicity and solubility.

Throughout this application when an alkyl substituent is identified, the normal alkyl structure is intended (i.e. butyl is n-butyl) unless otherwise specified. However, when radicals are identified (e.g. $R^5$), both branched and straight chains are included in the definition of alkyl, alkenyl, and alkynyl.

II. Compositions With Non-NMDA Receptor Antagonist Properties

A. Compounds of Formula I

Compounds of Formula I are provided which are active as non-NMDA ionotropic EAA receptor antagonists.

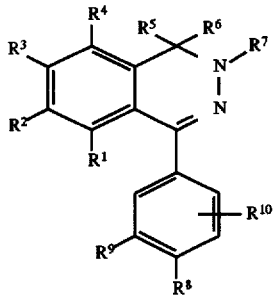

I wherein
$R^1$, $R^2$, $R^3$ and $R^4$ are independently
- a) H,
- b) HO,
- c) $R^{11}O$—,
- d) halogen (F, Cl, Br),
- e) C1–C3-alkyl,
- f) CF3,
- g) $R^{12}CO_2$—, or
- h) $R^{12}CONH$—;

$R^1$ and $R^2$, or $R^2$ and $R^3$, or $R^3$ and $R^4$ can be taken together to be
- a) —OCH$_2$O—, or
- b) —OCH$_2$CH$_2$O—;

$R^5$ and $R^6$ are independently
- a) H,
- b) C1–C6-alkyl,
- c) C3–C6-alkenyl,
- d) C3–C6-alkynyl,
- e) C3–C6-cycloalkyl,
- f) phenyl or substituted phenyl, where the phenyl is substituted with one or two substituents, C1–C3-alkyl, halogen (F, Cl, Br), $R^{12}HN$—, $R^{12}O$—, CF$_3$—, $R^{11}SO_2$— or CO$_2R^{12}$, or
- g) phenyl-C1–C3-alkyl or substituted phenyl-C1–C3-alkyl, where the phenyl is substituted with one or two substituents, C1–C3-alkyl, halogen (F, Cl, Br), $R^{12}HN$—, $R^{12}O$—, CF$_3$—, $R^{11}SO_2$— or , CO$_2R^{12}$;

$R^5$ and $R^6$ taken together can be C3–C6-cycloalkyl;

$R^7$ is
- a) $R^{13}R^{14}NCO$—,
- b) $R^{13}R^{14}NCS$—,
- c) $R^{13}R^{14}NC(NR^{12})$—,
- d) $R^{15}OCO$—
- e) $R^{13}CO$—
- f) $R^{13}R^{14}NCH_2CO$—,
- g) $R^{12}O_2C$—(CH$_2$)$_n$—,
- h) $R^{13}R^{14}NCO$—(CH$_2$)$_n$—,
- i) NC—(CH$_2$)$_n$—,
- j) H,
- k) C1–C6 alkyl,
- l) C1–C6-perfluoroalkyl,
- m) C3–C6-alkenyl,
- n) C3–C6-alkynyl, or
- o) C3–C6-cycloalkyl;

$R^6$ and $R^7$ taken together can be
- a) —(CH$_2$)$_m$CH$_2$(R$^{13}$)NCO—,
- b) —(CH$_2$)$_m$CH$_2$OCO—, or
- c) —(CH$_2$)$_m$CH$_2$CH$_2$CO—;

$R^8$ and $R^9$ are independently
- a) H,
- b) $R^{13}R^{14}N$—,
- c) $R^{13}NHC(NH)$,
- d) $R^{12}HNOC$—, or
- e) $R^{12}CONH$—;

$R^{10}$ is
- a) H,
- b) C1–C3-alkyl,
- c) halogen (F, Cl, Br),
- d) $R^{12}HN$—,
- e) $R^{12}O$—,
- f) CF$_3$—, or
- g) CO$_2R^{12}$;

$R^{11}$ is C1–C3-alkyl;

$R^{12}$ is H or C1–C3-alkyl;

$R^{13}$ and $R^{14}$ are independently
- a) H,
- b) C1–C10-alkyl,
- c) C1–C6-perfluoroalkyl,
- d) C3–C10-alkenyl,
- e) C3–C10-alkynyl, or
- f) C3–C6-cycloalkyl;

$R^{13}$ and $R^{14}$ taken together can be C3–C6-cycloalkyl;

$R^{15}$ is C1–C6-alkyl, C3–C6-alkenyl, or C3–C6-cycloalkyl;

n is 1 to 6;

m is 0 to 2;

and pharmaceutically acceptable salts thereof;

wherein $R^8$ and $R^9$ cannot both be H.

Preferred compounds are compounds of Formula I wherein:

$R^1$, $R^2$, $R^3$ and $R^4$ are independently H, $R^{11}O$—, halogen (F, Cl, Br), or C1–C3-alkyl;

$R^2$ and $R^3$ taken together can be —OCH$_2$O—;

$R^7$ is
- a) $R^{13}R^{14}NCO$—,
- b) $R^{13}R^{14}NC(NR^{12})$—,
- c) $R^{15}OCO$—,
- d) $R^{13}CO$—,
- e) $R^{13}R^{14}NCS$—, or
- f) H;

$R^8$ and $R^9$ are independently H, H$_2$N—, or CH$_3$CONH—;

and pharmaceutically acceptable salts thereof.

Specifically preferred are:

4-(4-aminophenyl)-1,2-dihydro-1-methyl-2-ethylcarbamoyl-6,7 methylenedioxyphthalazine, 4-(4-aminophenyl)-1,2-dihydro-1-methyl-2-propylcarbamoyl-6,7-methylenedioxyphthalazine, 4-(4-aminophenyl)-1,2-dihydro-1-methyl-2-n-butylcarbamoyl-6,7-methylenedioxyphthalazine, 4-(3-aminophenyl)-1,2-dihydro-1-methyl-2-n-butylcarbamoyl-6,7-methylenedioxyphthalazine, 4-(4-aminophenyl)-1,2-dihydro-1-methyl-2-propylthiocarbamoyl-6,7-methylenedioxyphthalazine, and 4-(4-acetylaminophenyl)-1,2-dihydro-1-methyl-6,7-methylenedioxyphthalazine.

The compounds of Formula I may be combined with a suitable pharmaceutical carrier and used to treat neurological, neuropsychological, neuropsychiatric, neurodegenerative, neuropsychopharmacological and functional disorders associated with excessive activation of the non-NMDA subtype of the ionotropic EAA receptors. The compounds can also be used as testing agents to identify and characterize other compounds for the treatment of acute and chronic neurodegenerative diseases, seizures, depression, anxiety and substance addiction.

B. Compounds of Formula II

In another embodiment, compounds of Formula II are provided which are active as non-NMDA ionotropic EAA receptor antagonists.

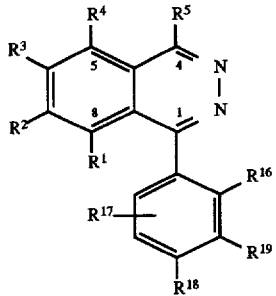

II wherein $R^1$, $R^2$, $R^3$ and $R^4$ are independently
  a) H,
  b) HO,
  c) $R^{11}O$—,
  d) halogen (F, Cl, Br),
  e) C1–C3-alkyl,
  f) $CF_3$,
  g) $R^{12}CO_2$—, or
  h) $R^{12}CONH$—;

$R^1$ and $R^2$, or $R^2$ and $R^3$, or $R^3$ and $R^4$ can be taken together to be
  a) —$OCH_2O$—, or
  b) —$OCH_2CH_2O$—;

$R^5$ is
  a) H,
  b) C1–C6-alkyl,
  c) C3–C6-alkenyl,
  d) C3–C6-alkynyl,
  e) C3–C6-cycloalkyl,
  f) phenyl or substituted phenyl, where the phenyl is substituted with one or two substituents selected from the group C1–C3-alkyl, halogen (F, Cl, Br), $R^{12}HN$—, $R^{12}O$—, $CF_3$—, $R^{11}SO_2$— or $CO_2R^{12}$, and
  g) phenyl-C1–C3-alkyl or substituted phenyl-C1–C3-alkyl, where the phenyl is substituted with one or two substituents selected from the group C1–C3-alkyl, halogen (F, Cl, Br), $R^{12}HN$—, $R^{12}O$—, $CF_3$—, $R^{11}SO_2$— or $CO_2R^{12}$;

$R^{11}$ is C1–C3-alkyl;
$R^{12}$ is H or C1–C3-alkyl;
$R^{16}$ or $R^{17}$ are independently
  a) H,
  b) C1–C3-alkyl,
  c) halogen (F, Cl, Br),
  d) $R^{12}O$—,
  e) $CF_3$—, or
  f) —$CO_2R^{12}$;

$R^{18}$ and $R^{19}$ are independently
  a) H,
  b) $R^{13}R^{14}N$—,
  c) $R^{13}NHC(NH)$, or
  d) $R^{12}COHN$—;

and pharmaceutically acceptable salts thereof, with the proviso that $R^{18}$ and $R^{19}$ cannot both be H.

Preferred compounds are compounds of Formula II wherein:

$R^1$, $R^2$, $R^3$ and $R^4$ are independently H, $R^{11}O$—, halogen (F, Cl, Br), or C1–C3-alkyl;

$R^2$ and $R^3$ taken together can be —$OCH_2O$—;

$R^{18}$ and $R^{19}$ are independently H, $NH_2$ or $CH_3CONH$—;.

and pharmaceutically acceptable salts thereof.

Specifically preferred are:

1-(3-aminophenyl)-6,7-methylenedioxyphthalazine, 1-(3-amino-4-methylphenyl)-6,7-methylenedioxyphthalazine, 1-(3-amino-4-chlorophenyl)-6,7-methylenedioxyphthalazine, 1-(3-aminophenyl)-6-methoxyphthalazine, 1-(3-amino-4-methylphenyl)-6-methoxyphthalazine, 1-(3-amino-4-chlorophenyl)-6-methoxyphthalazine 1-(4-aminophenyl)-6,7-methylenedioxyphthalazine, 1-(4-acetylaminophenyl)-6,7-methylenedioxyphthalazine, 4-(4-aminophenyl)-1-methyl-6,7-methylenedioxyphthalazine, 4-(4-acetylaminophenyl)-1-methyl-6,7-methylenedioxyphthalazine, 1-(4-aminophenyl)-7-methoxyphthalazine, 1-(4-acetylaminophenyl)-7-methoxyphthalazine, 4-(4-aminophenyl)-1-methyl-7-methoxyphthalazine, and 4-(4-acetylaminophenyl)-1-methyl-7-methoxyphthalazine.

The compounds of Formula II may be combined with a suitable pharmaceutical carrier and used to treat neurological, neuropsychological, neuropsychiatric, neurodegenerative, neuropsychopharmacological and functional disorders associated with excessive activation of the non-NMDA subtype of the ionotropic EAA receptors. The compounds can also be used as testing agents to identify and characterize other compounds for the treatment of acute and chronic neurodegenerative diseases, seizures, depression, anxiety and substance addiction.

III. Synthesis

The compounds of Formula I or II may be prepared using synthetic reactions and techniques available in the art, as described, for example in March, "Advanced Organic Chemistry," 4th Edition, 1992, Wiley-Interscience Publication, New York. The reactions are performed in solvent suitable to the reagents and materials employed and suitable for the transformation being effected. Depending upon the synthetic route selected, and the functionality of the starting material or intermediates, the appropriate protection groups and deprotection conditions available in the art of organic synthesis may be utilized in the synthesis of the compound.

In one embodiment, compounds of Formula I may be synthesized as outlined in Scheme 1. Protected aldehydes 3 can be prepared from commercially available aldehydes or aldehydes known in the literature by halogenating the aldehyde by treatment with bromine in a solvent such as acetic acid at a temperature from 0° to 35° C. for 6–24 hours. The aldehyde is then protected by a group such as an acetal by treatment of 2 with an alcohol such as ethylene glycol or ethanol in an inert solvent such as toluene with a

Scheme 1

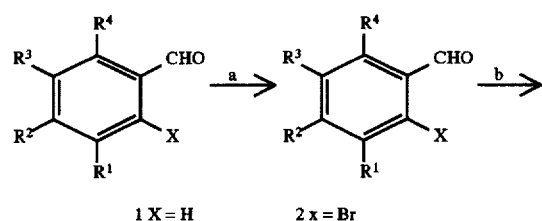

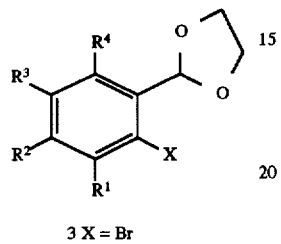

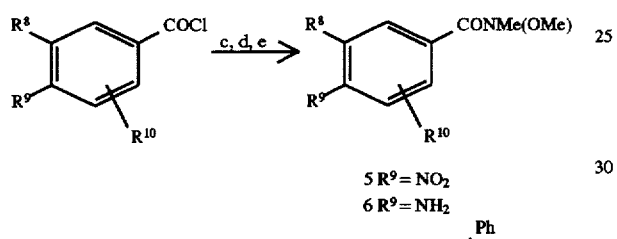

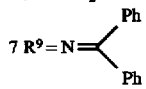

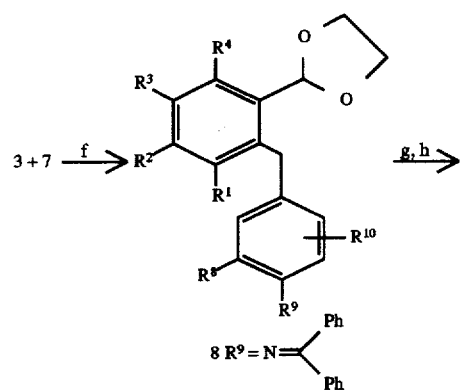

-continued
Scheme 1

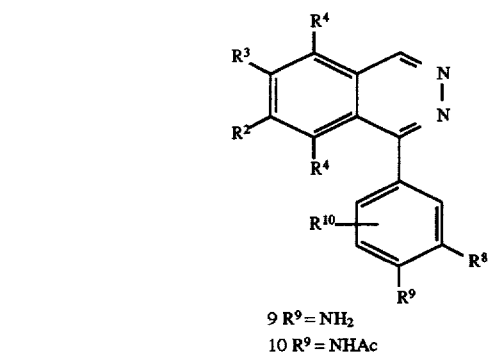

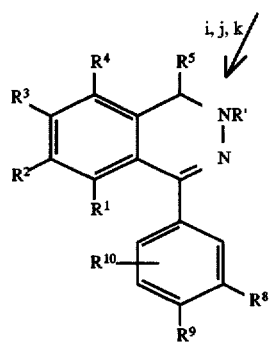

Reagents and Conditions: a) Br$_2$, AcOH;
b) Eth. glycol, TsOH, tol., reflux;c) HNMe(OMe) HCl. pyr., DCM;
d) H$_2$, Pd/C, MeOH; e) Benzophenoneimine, BF$_3$OEt$_2$, tol., reflux;
f) n-BuLi, THF, −78° C.; g) H$_2$NNH$_2$HCl, MeOH−H$_2$O; h) Ac$_2$O;
i) MeLi (Et$_2$O), TMEDA, THF, 0° C.; i) MeNCO, DCM;
k) 1NNaOH, MeOH.

catalytic amount of an acid such as p-toluensulfonic acid at the reflux temperature of the mixture with an apparatus to remove the water.

Protected amides 7 can be prepared from appropriate acids or acid chlorides by treatment of the acid chloride or acid anhydride with N,O-dimethylhydroxylamine in an inert solvent such as methylene chloride or tetrahydrofuran and a base such a pyridine at a temperature of −10° to 0° C. for 1–8 hours. Amides 6 can be converted to anilines by reducing the nitro group by treatment of 5 with hydrogen and a catalyst such a 10% Pd/C or 5% Pt/C in a solvent such as methanol at a pressure from atmospheric pressure to 60 psi for 30 minutes to 6 hours. The aniline 6 can be protected as the imine by treatment with a ketone such a benzophenone or an imine such as benzophenone imine in an inert solvent such as toluene with an acid catalyst such as boron trifluoride at a temperature from 20° C. to the reflux of the solvent for 2–8 hours.

The substituted benzophenones 8 are prepared by reacting the lithiated derivative of 3, which is generated by reacting 3 with a reagent such as n-butyl lithium in an inert solvent such as tetrahydrofuran at a temperature of –110° to –45° C. for 10–60 minutes, with amides 7 at a temperature of –78° to 25° C. for 2–24 hours. The benzophenones 8 are then converted to phthalazines 9 by treatment with hydrazine or hydrazine hydrochloride in a solvent such as methanol at a temperature of 0° to 35° C. for 6–24 hours. The phthalazine anilines 9 are protected by treatment with an amine protecting group such as acetic anhydride either neat or in an inert solvent such as tetrahydrofuran at a temperature of 0° C. to reflux of the solvent for 2–12 hours.

The dihydrophthalazines 11 are prepared by reacting protected phthalazine 10 with an alkyl lithium or Grignard reagent in an inert solvent such as tetrahydrofuran at a temperature of –78° to 25° C. for 1–6 hours. The dihydrophthalazines 11 can then be treated with an acylating reagent such as acid chloride, an alkylisocyanate, an alkylisothiocyanate, an alkylchloroformate or chloroamidate in an inert solvent such as methylene chloride with a base such as dimethylamino pyridine (DMAP) at a temperature of 0° C. to reflux of the solvent for 6–48 hours. The acetanilide protecting group can then be removed by careful treatment with an base such as NaOH in a solvent such as methanol at a temperature of 25° C. to reflux of the mixture for 2–72 hours.

Exemplary compounds of Formula I, Examples 1–135, which can be prepared using the above methods, as shown in Scheme 1 above, by using the appropriate starting materials and reagents, are listed below in Table 1. The synthesis of Examples 1, 2, 3, 4, 11, 23 and 31 is described below.

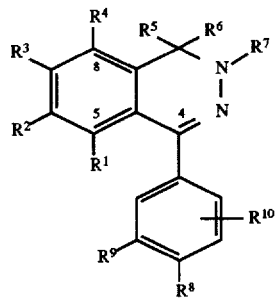

TABLE 1

Receptor Antagonists of Formula I.

| EX. | $R^1, R^2, R^3, R^4$ | $R^5, R^6$ | $R^7$ | $R^8, R^9R^{10}$ | Anal. |
|---|---|---|---|---|---|
| 1 | 6,7-methylenedioxy | Me, H | MeNHCO | 4-$NH_2$ | NMR, IR |
| 2 | 6,7-methylenedioxy | Me, H | EtNHCO | 4-$NH_2$ | NMR, IR |
| 3 | 6,7-methylenedioxy | Me, H | nPrNHCO | 4-$NH_2$ | NMR, IR |
| 4 | 6,7-methylenedioxy | Me, H | iPr NHCO | 4-$NH_2$ | NMR, IR |
| 5 | 6,7-methylenedioxy | Me, H | nBuNHCO | 4-$NH_2$ | NMR, IR |
| 6 | 6,7-methylenedioxy | Me, H | sBuNHCO | 4-$NH_2$ | |
| 7 | 6,7-methylenedioxy | Me, H | tBuNHCO | 4-$NH_2$ | NMR, IR |
| 8 | 6,7-methylenedioxy | Me, H | cyclopropylNHCO | 4-$NH_2$ | |
| 9 | 6,7-methylenedioxy | Me, H | $C_6H_{13}$NHCO | 4-$NH_2$ | |
| 10 | 6,7-methylenedioxy | Me, H | $H_2$NCO | 4-$NH_2$ | |
| 11 | 6,7-methylenedioxy | Et, H | MeNHCO | 4-$NH_2$ | NMR, IR |
| 12 | 6,7-methylenedioxy | n-Bu, H | EtNHCO | 4-$NH_2$ | |
| 13 | 6,7-methylenedioxy | Me, Me | EtNHCO | 4-$NH_2$ | |
| 14 | 6,7-methylenedioxy | cyclopropyl | EtNHCO | 4-$NH_2$ | |
| 15 | 6,7-methylenedioxy | cyclohexyl | EtNHCO | 4-$NH_2$ | |
| 16 | 6,7-methylenedioxy | CH3, H | EtNHCO | 4-$NH_2$ | |
| 17 | 6,7-methylenedioxy | Me, H | MeCO | 4-$NH_2$ | NMR, IR |
| 18 | 6,7-methylenedioxy | Me, H | EtCO | 4-$NH_2$ | |
| 19 | 6,7-methylenedioxy | Et, H | EtCO | 4-$NH_2$ | |
| 20 | 6,7-methylenedioxy | n-Bu, H | EtCO | 4-$NH_2$ | |
| 21 | 6,7-methylenedioxy | Me, Me | EtCO | 4-$NH_2$ | |
| 22 | 6,7-methylenedioxy | cyclopropyl | EtCO | 4-$NH_2$ | |
| 23 | 6,7-methylenedioxy | Me, H | MeOCO | 4-$NH_2$ | NMR, IR |
| 24 | 6,7-methylenedioxy | Me, H | EtOCO | 4-$NH_2$ | |
| 25 | 6,7-methylenedioxy | Et, H | EtOCO | 4-$NH_2$ | |
| 26 | 6,7-methylenedioxy | n-Bu, H | EtOCO | 4-$NH_2$ | |
| 27 | 6,7-methylenedioxy | Me, H | PhOCO | 4-$NH_2$ | |
| 28 | 6,7-methylenedioxy | cyclopropyl | EtOCO | 4-$NH_2$ | |
| 29 | 6,7-methylenedioxy | Me, H | iPrNHCO | 4-$NH_2$ | |
| 30 | 6,7-methylenedioxy | Me, H | nPrNHCO | 4-$NH_2$ | |
| 31 | 6,7-methylenedioxy | Me, H | $Me_2$NCO | 4-$NH_2$ | NMR, IR |
| 32 | 6-methoxy | Me, H | $Me_2$NCO | 4-$NH_2$ | |
| 33 | 6-methoxy | Me, H | $Et_2$NCO | 4-$NH_2$ | |
| 34 | 6-methoxy | Et, H | $Me_2$NCO | 4-$NH_2$ | |
| 35 | 6-methoxy | n-Bu, H | $Me_2$NCO | 4-$NH_2$ | |
| 36 | 6-methoxy | Me, Me | $Me_2$NCO | 4-$NH_2$ | |
| 37 | 6-methoxy | cyclopropyl | $Me_2$NCO | 4-$NH_2$ | |
| 38 | 6-methoxy | cyclohexyl | $Me_2$NCO | 4-$NH_2$ | |
| 39 | 6-methoxy | CH3, H | $Me_2$NCO | 4-$NH_2$ | |
| 40 | 6-methoxy | Me, H | MeCO | 4-$NH_2$ | |
| 41 | 6-methoxy | Me, H | EtCO | 4-$NH_2$ | |
| 42 | 6-methoxy | Et, H | EtCO | 4-$NH_2$ | |
| 43 | 6-methoxy | n-Bu, H | EtCO | 4-$NH_2$ | |
| 44 | 6-methoxy | Me, Me | EtCO | 4-$NH_2$ | |

TABLE 1-continued

Receptor Antagonists of Formula I.

| EX. | $R^1, R^2, R^3, R^4$ | $R^5, R^6$ | $R^7$ | $R^8, R^9R^{10}$ | Anal. |
|---|---|---|---|---|---|
| 45 | 6-methox.y | cyclopropyl | EtCO | 4-$NH_2$ | |
| 46 | 6-methoxy | Me, H | MeOCO | 4-$NH_2$ | |
| 47 | 6-methoxy | Me, H | EtOCO | 4-$NH_2$ | |
| 48 | 6-methoxy | Et, H | EtOCO | 4-$NH_2$ | |
| 49 | 6-methoxy | n-Bu, H | EtOCO | 4-$NH_2$ | |
| 50 | 6-methoxy | Me, Me | EtOCO | 4-$NH_2$ | |
| 51 | 6-methoxy | cyclopropyl | EtOCO | 4-$NH_2$ | |
| 52 | 6-methoxy | Me, H | iPrNHCO | 4-$NH_2$ | |
| 53 | 6-methoxy | Me, H | nPrNHCO | 4-$NH_2$ | |
| 54 | 6,7-methylenedioxy | Me, H | MeNHCO | 3-$NH_2$ | |
| 55 | 6,7-methylenedioxy | Me, H | EtNHCO | 3-$NH_2$ | |
| 56 | 6,7-methylenedioxy | Me, H | nPrNHCO | 3-$NH_2$ | |
| 57 | 6,7-methylenedioxy | Me, H | nBuNHCO | 3-$NH_2$ | |
| 58 | 6,7-methylenedioxy | Me, H | MeCO | 3-$NH_2$ | |
| 59 | 6,7-methylenedioxy | Me, H | MeNHCO | 3-MeO,4-$NH_2$ | |
| 60 | 6,7-methylenedioxy | Me, H | EtNHCO | 3-MeO,4-$NH_2$ | |
| 61 | 6,7-methylenedioxy | Me, H | MeCO | 3-MeO,4-$NH_2$ | |
| 62 | 6,7-methylenedioxy | Me, H | EtCO | 3-MeO,4-$NH_2$ | |
| 63 | 6,7-methylenedioxy | Me, H | EtCO | 3-$NH_2$ | |
| 64 | 6,7-methylenedioxy | Me, H | MeNHCO | 3-Cl,4-$NH_2$ | |
| 65 | 6,7-methylenedioxy | Me, H | EtNHCO | 3-Cl,4-$NH_2$ | |
| 66 | 6,7-methylenedioxy | Me, H | MeCO | 3-Cl,4-$NH_2$ | |
| 67 | 6,7-methylenedioxy | Me, H | EtCO | 3-Cl,4-$NH_2$ | |
| 68 | 6-methoxy | Me, H | EtNHCO | 4-$NH_2$ | |
| 69 | 6-methoxy | Me, H | nBuNHCO | 4-$NH_2$ | |
| 70 | 6-methoxy-7-chloro | Me, H | EtNHCO | 4-$NH_2$ | |
| 71 | 6-methoxy-7-chloro | Me, H | nPrNHCO | 4-$NH_2$ | |
| 72 | 7-methoxy | Me, H | EtNHCO | 4-$NH_2$ | |
| 73 | 7-methoxy | Me, H | nPrNHCO | 4-$NH_2$ | |
| 74 | 6-chloro-7-methoxy | Me, H | EtNHCO | 4-$NH_2$ | |
| 75 | 6-chloro-7-methoxy | Me, H | nPrNHCO | 4-$NH_2$ | |
| 76 | 6-methoxy-7-methyl | Me, H | nPrNHCO | 4-$NH_2$ | |
| 77 | 6,7-methylenedioxy | Me, H | MeNHCS | 4-$NH_2$ | |
| 78 | 6,7-methylenedioxy | Me, H | EtNHCS | 4-$NH_2$ | |
| 79 | 6,7-methylenedioxy | Me, H | nPrNHCS | 4-$NH_2$ | NMR, IR |
| 80 | 6,7-methylenedioxy | Me, H | iPr NHCS | 4-$NH_2$ | |
| 81 | 6,7-methylenedioxy | Me, H | nBuNHCS | 4-$NH_2$ | |
| 82 | 6,7-methylenedioxy | Me, H | sBuNHCS | 4-$NH_2$ | |
| 83 | 6,7-methylenedioxy | Me, H | tBuNHCS | 4-$NH_2$ | |
| 84 | 6,7-methylenedioxy | Me, H | cyclopropylNHCS | 4-$NH_2$ | |
| 85 | 6,7-methylenedioxy | Me, H | $C_6H_{13}$NHCS | 4-$NH_2$ | |
| 86 | 6,7-methylenedioxy | Me, H | $H_2$NCS | 4-$NH_2$ | |
| 87 | 6,7-methylenedioxy | Et, H | MeNHCS | 4-$NH_2$ | |
| 88 | 6,7-methylenedioxy | n-Bu, H | EtNHCS | 4-$NH_2$ | - |
| 89 | 6,7-methylenedioxy | Me, Me | EtNHCS | 4-$NH_2$ | |
| 90 | 6,7-methylenedioxy | cyclopropyl | EtNHCS | 4-$NH_2$ | |
| 91 | 6,7-methylenedioxy | cyclohexyl | EtNHCS | 4-$NH_2$ | |
| 92 | 6,7-methylenedioxy | CH3, H | EtNHCS | 4-$NH_2$ | |
| 93 | 6,7-methylenedioxy | Me, H | MeNHCO | 3-$NH_2$ | |
| 94 | 6,7-methylenedioxy | Me, H | EtNHCO | 3-$NH_2$ | |
| 95 | 6,7-methylenedioxy | Me, H | nPrNHCO | 3-$NH_2$ | |
| 96 | 6,7-methylenedioxy | Me, H | iPrNHCO | 3-$NH_2$ | |
| 97 | 6,7-methylenedioxy | Me, H | nBuNHCO | 3-$NH_2$ | |
| 98 | 6,7-methylenedioxy | Me, H | sBUNHCO | 3-$NH_2$ | |
| 99 | 6,7-methylenedioxy | Me, H | tBuNHCO | 3-$NH_2$ | |
| 100 | 6,7-methylenedioxy | Me, H | cyclopropylNHCO | 3-$NH_2$ | |
| 101 | 6,7-methylenedioxy | Me, H | $C_3H_{16}$NHCO | 3-$NH_2$ | |
| 102 | 6,7-methylenedioxy | Me, R | $H_2$NCO | 3-$NH_2$ | |
| 103 | 6,7-methylenedioxy | Et, H | MeNHCO | 3-$NH_2$ | |
| 104 | 6,7-methylenedioxy | nBu, R | EtNHCO | 3-$NH_2$ | |
| 105 | 6,7-methylenedioxy | Me, Me | EtNHCO | 3-$NH_2$ | |
| 106 | 6,7-methylenedioxy | cyclopropyl | EtNHCO | 3-$NH_2$ | |
| 107 | 6,7-methylenedioxy | cyclohexyl | EtNHCO | 3-$NH_2$ | |
| 108 | 6,7-methylenedioxy | $CH_3$, H | EtNHCO | 3-$NH_2$ | |
| 109 | H,H,H,H | Me, H | MeNHCO | 4-$NH_2$ | |
| 110 | H,H,H,H | Me, H | EtNHCO | 4-$NH_2$ | |
| 112 | H,H,H,H | Me, H | nPrNHCO | 4-$NH_2$ | |
| 113 | H,H,H,H | Me, H | iPrNHCO | 4-$NH_2$ | |
| 114 | H,H,H,H | Me, H | nBuNHCO | 4-$NH_2$ | |
| 115 | H,H,H,H | Me, H | sBuNHCO | 4-$NH_2$ | |
| 116 | H,H,H,H | Me, H | tBuNHCO | 4-$NH_2$ | |
| 117 | H,H,H,H | Me, H | cyclopropylNHCO | 4-$NH_2$ | |
| 118 | H,H,H,H | Me, H | $C_6H_{13}$NHCO | 4-$NH_2$ | |
| 119 | H,H,H,H | Me, H | $H_2$NCO | 4-$NH_2$ | |
| 120 | H,H,H,H | Et, H | MeNHCO | 4-$NH_2$ | |

TABLE 1-continued

Receptor Antagonists of Formula I.

| EX. | $R^1, R^2, R^3, R^4$ | $R^5, R^6$ | $R^7$ | $R^8, R^9R^{10}$ | Anal. |
|---|---|---|---|---|---|
| 121 | H,H,H,H | n-Bu, H | EtNHCO | 4-NH$_2$ | |
| 122 | H,H,H,H | Me, Me | EtNHCO | 4-NH$_2$ | |
| 123 | H,H,H,H | cyclopropyl | EtNHCO | 4-NH$_2$ | |
| 124 | H,H,H,H | cyclohexyl | EtNHCO | 4-NH$_2$ | |
| 125 | H,H,H,H | CH$_3$, H | EtNHCO | 4-NH$_2$ | |
| 126 | 6,7-methylenedioxy | Me, H | H | 4-CH$_3$CONH | NMR, IR |
| 127 | 6,7-methylenedioxy | Et, H | H | 4-CH$_3$CONH | |
| 128 | 6,7-methylenedioxy | n-Bu, H | H | 4-CH$_3$CONH | |
| 129 | 6,7-methylenedioxy | Me, Me | H | 4-CH$_3$CONH | |
| 130 | 6,7-methylenedioxy | cyclopropyl | H | 4-CH$_3$CONH | |
| 131 | 6,7-methylenedioxy | Me, H | H | 4-NH$_2$ | |
| 132 | 6,7-methoxy | Me, H | H | 4-CH$_3$CONH | |
| 133 | 6,7-methoxy | Me, H | CH$_3$CH$_2$CH$_2$NHCO | 4-NH$_2$ | NMR, IR |
| 134 | 6,7-methoxy | Me, H | Me | 4-CH$_3$CONH | |
| 135 | 6,7-methoxy | Et, H | Bu | 4-CH$_3$CONH | |

In another embodiment, exemplary compounds of Formula II, Examples 136–239, listed in Table 2, are provided, which can be prepared using the above methods using the appropriate starting materials and reagents. The synthesis of Example 185 is described below.

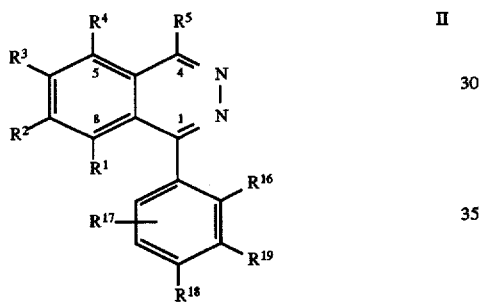

II

TABLE 2

Receptor Antagonists of Formula II.

| EX. | $R^1,R^2,R^3,R^4$ | $R^5$ | $R^{16},R^{17}$ | $R^{18},R^{19}$ | Anal. |
|---|---|---|---|---|---|
| 136 | 6,7-methylenedioxy | H | H,H | 3-NH$_2$ | NMR,IR |
| 137 | 6,7-methylenedioxy | Me | H,H | 3-NH$_2$ | |
| 138 | 6,7-methylenedioxy | Et | H,H | 3-NH$_2$ | |
| 139 | 6,7-methylenedioxy | Bu | H,H | 3-NH$_2$ | |
| 140 | 6,7-methylenedioxy | H | H,H | 3-NH$_2$ | |
| 141 | 6,7-methylenedioxy | Me | H,H | 3-NH$_2$ | |
| 142 | 6,7-methylenedioxy | Et | H,H | 3-NH$_2$ | |
| 143 | 6,7-methylenedioxy | Bu | H,H | 3-NH$_2$ | |
| 144 | 6,7-methylenedioxy | H | 5-Cl,H | 3-NH$_2$ | |
| 145 | 6,7-methylenedioxy | Me | 5-Cl,H | 3-NH$_2$ | |
| 146 | 6,7-methylenedioxy | Et | 5-Cl,H | 3-NH$_2$ | |
| 147 | 6,7-methylenedioxy | Bu | 5-Cl,H | 3-NH$_2$ | |
| 148 | 6,7-methylenedioxy | H | 5-MeO,H | 3-NH$_2$ | |
| 149 | 6,7-methylenedioxy | Me | 5-MeO,H | 3-NH$_2$ | |
| 150 | 6,7-methylenedioxy | Et | 5-MeO,H | 3-NH$_2$ | |
| 151 | 6,7-methylenedioxy | Bu | 5-MeO,H | 3-NH$_2$ | |
| 152 | 7-methoxy | H | H,H | 3-NH$_2$ | |
| 153 | 7-methoxy | Me | H,H | 3-NH$_2$ | |
| 154 | 7-methoxy | Et | H,H | 3-NH$_2$ | |
| 155 | 7-methoxy | Bu | H,H | 3-NH$_2$ | |
| 156 | 7-methoxy | H | H,H | 3-NH$_2$ | |
| 157 | 7-methoxy | Me | H,H | 3-NH$_2$ | |
| 158 | 7-methoxy | Et | H,H | 3-NH$_2$ | |
| 159 | 7-methoxy | Bu | H,H | 3-NH$_2$ | |
| 160 | 7-methoxy | H | 5-Cl,H | 3-NH$_2$ | |

TABLE 2-continued

Receptor Antagonists of Formula II.

| EX. | $R^1,R^2,R^3,R^4$ | $R^5$ | $R^{16},R^{17}$ | $R^{18},R^{19}$ | Anal. |
|---|---|---|---|---|---|
| 161 | 7-methoxy | Me | 5-Cl,H | 3-NH$_2$ | |
| 162 | 7-methoxy | Et | 5-Cl,H | 3-NH$_2$ | |
| 163 | 7-methoxy | Bu | 5-Cl,H | 3-NH$_2$ | |
| 164 | 7-methoxy | H | 5-MeO,H | 3-NH$_2$ | |
| 165 | 7-methoxy | Me | 5-MeO,H | 3-NH$_2$ | |
| 166 | 7-methoxy | Et | 5-MeO,H | 3-NH$_2$ | |
| 167 | 7-methoxy | Bu | 5-Meo,H | 3-NH$_2$ | |
| 168 | 7-methyl | H | H,H | 3-NH$_2$ | |
| 169 | 7-methyl | Me | H,H | 3-NH$_2$ | |
| 170 | 7-methyl | Et | H,H | 3-NH$_2$ | |
| 171 | 7-methyl | Bu | H,H | 3-NH$_2$ | |
| 172 | 7-methyl | H | H,H | 3-NH$_2$ | |
| 173 | 7-methyl | Me | H,H | 3-NH$_2$ | |
| 174 | 7-methyl | Et | H,H | 3-NH$_2$ | |
| 175 | 7-methyl | Bu | H,H | 3-NH$_2$ | |
| 176 | 7-methyl | H | 5-Cl,H | 3-NH$_2$ | |
| 177 | 7-methyl | Me | 5-Cl,H | 3-NH$_2$ | |
| 178 | 7-methyl | Et | 5-Cl,H | 3-NH$_2$ | |
| 179 | 7-methyl | Bu | 5-Cl,H | 3-NH$_2$ | |
| 170 | 7-methyl | H | 5-MeO,H | 3-NH$_2$ | |
| 181 | 7-methyl | Me | 5-MeO,H | 3-NH$_2$ | |
| 182 | 7-methyl | Et | 5-MeO,H | 3-NH | |
| 183 | 7-methyl | Bu | 5-MeO,H | 3-NH$_2$ | |
| 184 | 6,7-methylenedioxy | H | H,H | 4-NH$_2$ | NMR,IR |
| 185 | 6,7-methylenedioxy | Me | H,H | 4-NH$_2$ | NMR,IR |
| 186 | 6,7-methylenedioxy | Et | H,H | 4-NH$_2$ | |
| 187 | 6,7-methylenedioxy | Bu | H,H | 4-NH$_2$ | |
| 188 | 6,7-methylenedioxy | H | H,H | 4-NH$_2$ | |
| 189 | 6,7-methylenedioxy | Me | H,H | 4-NH$_2$ | |
| 190 | 6,7-methylenedioxy | Et | H,H | 4-NH$_2$ | |
| 191 | 6,7-methylenedioxy | Bu | H,H | 4-NH$_2$ | |
| 192 | 6,7-methylenedioxy | H | 5-Cl,H | 4-NH$_2$ | |
| 193 | 6,7-methylenedioxy | Me | 5-Cl,H | 4-NH$_2$ | |
| 194 | 6,7-methylenedioxy | Et | 5-Cl,H | 4-NH$_2$ | |
| 195 | 6,7-methylenedioxy | Bu | 5-Cl,H | 4-NH$_2$ | |
| 196 | 6,7-methylenedioxy | H | 5-MeO,H | 4-NH$_2$ | |
| 197 | 6,7-methylenedioxy | Me | 5-MeO,H | 4-NH$_2$ | |
| 198 | 6,7-methylenedioxy | Et | 5-MeO,H | 4-NH$_2$ | |
| 199 | 6,7-methylenedioxy | Bu | 5-MeO,H | 4-NH$_2$ | |
| 200 | 7-methoxy | H | H,H | 4-NH$_2$ | |
| 201 | 7-methoxy | Me | H,H | 4-NH$_2$ | |
| 202 | 7-methoxy | Et | H,H | 4-NH$_2$ | |
| 203 | 7-methoxy | Bu | H,H | 4-NH$_2$ | |
| 204 | 7-methoxy | H | H,H | 4-NH$_2$ | |
| 205 | 7-methoxy | Me | H,H | 4-NH$_2$ | |
| 206 | 7-methoxy | Et | H,H | 4-NH$_2$ | |
| 207 | 7-methoxy | Bu | H,H | 4NH$_2$ | |
| 208 | 7-methoxy | H | 5-Cl,H | 4-NH$_2$ | |
| 209 | 7-methoxy | Me | H,H | 4-NH$_2$ | |
| 200 | 7-methoxy | Et | 5-Cl,H | 4-NH$_2$ | |
| 211 | 7-methoxy | Bu | 5-Cl,H | 4-NH$_2$ | |
| 212 | 7-methoxy | H | 5-MeO,H | 4-NH$_2$ | |
| 213 | 7-methoxy | Me | 5-MeO,H | 4-NH$_2$ | |
| 214 | 7-methoxy | Et | 5-MeO,H | 4-NH$_2$ | |
| 215 | 7-methoxy | Bu | 5-MeO,H | 4-NH$_2$ | |
| 216 | 7-methyl | H | H,H | 4-NH$_2$ | |
| 217 | 7-methyl | Me | H,H | 4-NH$_2$ | |
| 218 | 7-methyl | Et | H,H | 4-NH$_2$ | |
| 219 | 7-methyl | Bu | H,H | 4-NH$_2$ | |
| 220 | 7-methyl | H | H,H | 4-NH$_2$ | |
| 221 | 7-methyl | Me | H,H | 4-NH$_2$ | |
| 222 | 7-methyl | Et | H,H | 4-NH$_2$ | |
| 223 | 7-methyl | Bu | H,H | 4-NH$_2$ | |
| 224 | 7-methyl | H | 5-Cl,H | 4-NH$_2$ | |
| 225 | 7-methyl | Me | 5-Cl,H | 4-NH$_2$ | |
| 226 | 7-methyl | Et | 5-Cl,H | 4-NH$_2$ | |
| 227 | 7-methyl | Bu | 5-Cl,H | 4-NH$_2$ | |
| 228 | 7-methyl | H | 5-MeO,H | 4-NH$_2$ | |
| 229 | 7-methyl | Me | 5-MeO,H | 4-NH$_2$ | |
| 230 | 7-methyl | Et | 5-MeO,H | 4-NH$_2$ | |
| 231 | 7-methyl | Bu | 5-MeO,H | 4-NH$_2$ | |
| 232 | 6,7-methylenedioxy | H | H,H | 4-NHMe | |
| 233 | 6,7-methylenedioxy | Me | H,H | 4-NHMe | |
| 234 | 6,7-methylenedioxy | Et | H,H | 4-NHMe | |
| 235 | 6,7-methylenedioxy | Bu | H,H | 4-NHMe | |

TABLE 2-continued

Receptor Antagonists of Formula II.

| EX. | $R^1,R^2,R^3,R^4$ | $R^5$ | $R^{16},R^{17}$ | $R^{18},R^{19}$ | Anal. |
|---|---|---|---|---|---|
| 236 | 6,7-methylenedioxy | H | H,H | 4-CH$_3$CONH | NMR,IR |
| 237 | 6,7-methylenedioxy | Me | H,H | 4-CH$_3$CONH | NMR,IR |
| 238 | 6,7-methylenedioxy | Et | H,H | 4-CH$_3$CONH | |
| 239 | 6,7-methylenedioxy | Bu | H,H | 4-CH$_3$CONH | |

IV. IN VITRO AND IN VIVO ASSAYS OF ACTIVITY AND THERAPEUTIC EFFICACY

In vivo and in vitro assays may be conducted to determine the activity of the compounds as antagonists of the non-NMDA receptors, i.e., the ionotropic EAA receptors which bind AMPA or KA. In combination, in vitro and in vivo assays are predictive of the activity of these compounds for treatment of patients. This is supported, for example, by numerous studies in the literature illustrating that in vitro and in vivo studies of NMDA receptor modulation by a test compound provide a good indication of the compound's efficacy in treating disorders associated with excessive activation of the NMDA receptor. See, e.g.: Meldrum, *Epilepsy Research*, 12:189–196 (1992); Lipton and Rosenberg, *New England Journal of Medicine*, 330:613–622 (1994); and McBurney, *Neurobiology of Aging*, 15:271–273 (1994).

Electrophysiology

The potency of Examples 1–5, 7, 11, 17 and 31 listed in Table 1, for drug inhibition of the AMPA receptor was tested using the whole-cell patch clamp technique on primary cultures of rat neocortex. The general procedure for stimulating AMPA-receptor mediated currents with KA and for the measurement of current inhibition is based on that used by Donevan and Rogawski (*Neuron*, 10:51–59, 1993) for 2,3-benzodiazepines.

Standard extracellular bath solutions and intracellular pipette solutions are used as described in detail by Hussy and coworkers (*J. Physiol.* (Lond.), 481.2:311–323,1994). The drug application system is designed to allow rapid switching between 7 different reservoirs containing either control bath solution, kainic acid (50 µM), or kainic acid (50 µM) plus antagonist (10 µM). Each recording is begun with a control response to KA alone.

Following the establishment of a 2–3 sec duration steady baseline, bathing solution is switched to one containing KA plus antagonist for an additional 2–3 sec period. Alternatively, 5 different doses of a single compound are tested for the determination of the antagonist IC$_{50}$. The results of the assay of Examples 1–5, 7, 11, 17 and 31 are listed below in Table 3, which illustrates AMPA receptor inhibition in rat cortical neurons. The compounds tested all were useful as antagonists of non-NMDA EAA receptors. All of the compounds tested were found to have a % inhibition ≧20 at a dose of 10 µM. Compounds which have a percent inhibition of greater than or equal to about 20% at a dose of about 10 µM are generally useful antagonists of the non-NMDA EAA receptors as disclosed herein.

TABLE 3

Inhibition of AMPA Binding to Receptor.

| EXAMPLE | AMPA % INHIBITION (10 µM drug) | AMPA IC50 µM |
|---|---|---|
| 1 | 20 | 23 |
| 2 | 55 | 7.2 |
| 3 | 80 | 2.8 |
| 4 | 45 | — |
| 5 | 86 | 1.8 |
| 7 | 70 | 5.4 |
| 11 | 36 | — |
| 17 | 20 | — |
| 31 | 33 | — |

Neurodegenerative Transient Global Forebrain Ischemia

The extent of protection by a test compound in a model of brain ischemia may be assayed as described by Meldrum et al. (*Brain Res.*, 571:115, 1992), and references cited therein. Male Wistar rats (250–300 g) are anesthetized using halothane-oxygen-nitrogen mixture and both vertebral arteries are permanently occluded by electrocauterisation within the alar foraminae of the first cervical vertebra. At the same time, both common carotid arteries are isolated and atraumatic clamps placed around each one. One femoral vein is cannulated to enable the subsequent iv administration of fluid. The following day cerebral ischemia is induced in the unanaesthetised animal, by tightening the clamps around the carotid arteries for 20 min. Carotid clamping results. Body temperature is maintained at 37° C. by use of a rectal probe and hot plate. Seven days after the ischemic insult rats are sacrificed and the brains processed for light microscopy. Neuroprotection is assessed by examination of the extent of damage in the cortex and hippocampus. Compounds may be selected which are active in this model.

Neurodegenerative Permanent Focal Ischemia

The extent of protection by a test compound in a model of brain ischemia may be tested using a model described by Meldrum and Smith (*Stroke*, 23:861, 1992), and references cited therein. Male Fisher F344 rats (210–310 g) are anesthetized with halothane-oxygen-nitrogen mixture receive a small incision between the eye and ear, the mandibular muscles are retracted to expose the orbit and zygomatic arch. A small craniotomy is made to expose the base of the middle cerebral artery. Bipolar coagulation is used to permanently occlude the artery at the base. One day after the ischemic insult rats are sacrificed and the brains processed for light microscopic examination. Lesion volume is determined by using Cavalarei's principle. Compounds may be selected which are active in this model.

Maximum Electro Shock (MES) Seizure Test

The extent of protection by a test compound in a seizure model is tested as described by Rogawski et al. (*Epilepsy Research*, 15:179–184, 1993). Male NIH Swiss mice (25–30 g) are injected ip with the test drug. The mice are subjected to a 0.2 sec, 60 Hz, 50 mA electrical stimulus delivered with corneal electrodes wetted with 0.9% saline at 15–30 min post dosing. Animals failing to show tonic hind limb extension are scored as protected. Compounds may be selected which are active in this model.

The results of this assay using the compounds, Examples 2, 3, and 133 are shown below in Table 4.

TABLE 4

MES Test Results

| Example | Dose (mg/kg) | Time (hours) | Score (protected/ no. tested) |
|---|---|---|---|
| 2 | 30 | 0.5 | 3/3 |
| 3 | 31 | 0.5 | 5/8 |
| 133 | 30 | 0.5 | 1/3 |

Subcutaneous Metrazol (scMET) Seizure Test

This test is to determine the extent of protection by a test compound in a seizure model. The method used is that of Chen et at. (*Proc. Soc. Exp. Biol. Med.*, 87:334, 1954). Mice are randomly assigned to vehicle or treatment groups of 3–10 animals per group and then dosed accordingly. Metrazol (pentylenetetrazol) 90 mg/kg is administered subcutaneously (sc) at different time points (0.25, 0.5, 1, 2, 4 hr) after the treatment or control groups. The mice individually housed in clear runs and observed for the presence or absence of clonic seizure activity (>5 s duration) for 30 min after metrazol dosing. A compound is considered active if no seizure is observed. Data is analyzed using a quantal measure (protection/number tested).

The results of this assay using the compound, Example 133, is shown below in Table 5.

TABLE 5 scMET Test Results

| Example | Dose (mg/kg) | Time (hr) | Score (protect./no. tested) |
|---|---|---|---|
| 133 | 30 | 0.5 | 1/5 |

The compounds can be administered parenterally, i.e., subcutaneously, intramuscularly, or intravenously and, alternatively, administered orally, in a dose range of between about 0.01 and 100 mg/kg body weight.

The active ingredient can be administered parenterally in sterile liquid dosage forms. In general, water, a suitable oil, saline, aqueous dextrose, and related sugar solutions and glycols such as propylene glycol or polyethylene glycols are suitable carriers for parenteral solutions. Solutions for parenteral administration preferably contain a water soluble form of the active ingredient, suitable stabilizing agents, and, if necessary, buffer substances. Antioxidizing agents such as sodium bisulfite, sodium sulfite, or ascorbic acid either alone or combined are suitable stabilizing agents. Also solutions can contain preservatives, such as benzalkonium chloride, methyl- or propylparaben, and chlorobutanol.

The active ingredient can be administered orally in solid dosage forms, such as capsules, tablets and powders, or in liquid dosage forms, such as elixirs, syrups, and suspensions. Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. The active ingredients also may be provided in a particle for sustained or pulsed delivery such as a liposome or microcapsule. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. Suitable pharmaceutical carriers are described in Remington's Pharmaceutical Sciences, a standard reference text in this field.

Optionally, the compounds either alone or in combination with a carrier may be administered by implantation or by application to a mucosal surface, for example, the nasal-pharyngeal region and/or lungs using an aerosol or may be administered to a skin surface via a topical carrier such as a cream or lotion.

The compounds of this invention and their preparation can be understood further by the following non-limiting examples which describe the synthesis of exemplary compounds of Formula I (see Table D. In these examples, unless otherwise indicated, all temperatures are in degrees Celsius and parts and percentages are by weight.

EXAMPLE 1

Preparation of 4-(4-Aminophenyl)-1,2-dihydro-1-methyl-2-(N"-methylcarbamoyl)-6,7-methylendioxyphthalazine Part A: Preparation of 1-Bromo-3,4-methylendioxy-benzaldehyde Piperanal (30 g 0.20 mole) was dissolved in acetic acid (200 mL and treated with a solution of bromine (80 g, 0.50 mole) in acetic acid (100 mL). The solution stirred at ambient temperature for 24 h and then water (300 mL) was added. After stirring for 15 minutes the solid precipitate was collected by filtration, washed with water and recrystallized from 10% aqueous methanol (450 mL). The resultant solid weighed 23 g (50%). Mp 123°–5° C. IR (PTFE Film); 1672 $cm^{-1}$, 1610, 1487, 1112, 923, 887.

Part B: Preparation of 5-Bromo-6-(1,3-dioxolanyl-2-yl)-2,3-methylenedioxybenzene A mixture of 5-Bromo-3,4-methylendioxy-benzaldehyde (16 g, 70 mmole), ethylene glycol (8.7 g, 0.14 mole), toluensulfonic acid monohydrate (0.50 g) and toluene (450 mL) were stirred rapidly and heated to reflux while water was removed with a Dean-Stark apparatus. After one hour the mixture was cooled to 20° C., washed with water (200 mL) and aqueous saturated sodium bicarbonate (100 mL), dried (MgSO$_4$) and evaporated in vacuo to leave a yellow oil. The oil was crystallized from hexanes-EtOAc to afford a beige solid (8.9 g, 47%). The filtrate was concentrated and chromatographed on silica gel eluting with 20% EtOAc/hexanes to 25% EtOAc/hexanes. The isolated oil was crystallized from hexanes-EtOAc to leave an additional 4.8 g. Total yield=13.7 g (72%). Mp 69°–71° C. 200 MHz $^1$H-NMR (CDCl$_3$); δ7.10 (s, 1H), 7.00 (s, 1H), 6.08 (s, 1H, ArCH), 6.00 (s, 2H), 4.12 (m, 4H, OCH$_2$CH$_2$O): IR (PTFE film); 1503 $cm^{-1}$, 1471, 1241, 1036.

Part C: Preparation of N'-Methoxyl-N'-methyl-4-nitrobenzenecarboxamide

A mixture of p-nitrobenzoyl chloride (30 g, 0.16 mole), N,O,-dimethylhydroxylamine hydrochloride (17 g, 0.18 mole) and methylene chloride (500 mL) were stirred and cooled in an ice bath. Pyridine (28 g, 0.36 mole) was added dropwise over 5 minutes and the mixture stirred an additional 2 hours. The solvents were evaporated in vacuo, the residue was treated with EtOAc (300 mL) and 1N HCl (100 mL) and separated. The aqueous layer was washed with EtOAc (100 mL), the combined organic layers were dried ($MgSO_4$) and evaporated in vacuo to leave a yellow oil that crystallized upon treatment with ether-hexanes. The light yellow solid was collected by filtration, washed (ether-hexanes) and air dried to afford 24 g (71%) of the amide. Mp 71°–74° C.

Part D: Preparation of N'-Methoxyl-N'-methyl-4-aminobenzenecarboxamide

N'-Methoxyl-N'-methyl-4-nitrobenzenecarboxamide (22 g, 0.10 mole), 10% palladium on carbon (1.0 g) and methanol (500 mL) were agitated on a Parr shaker under 45 p.s.i. initial pressure. After 30 minutes no more hydrogen uptake was observed. The catalyst was filtered, washed (methanol) and the filtrate was evaporated in vacuo to afford a tan solid. The solid was chromatographed on silica gel eluting with a gradient of 33% hexanes/EtOAc to 25% hexanes/EtOAc. The amine was obtained as a tan solid (19 g, 100%). Mp 91°–94° C. 200 MHz $^1$H-NMR ($CDCl_3$); $\delta$7.63 (d, 2H, J=8.4 Hz, $H^2$), 6.66 (d, 2H, J=8.4 Hz, $H_3$), 3.95 (bs, 2H, $NH_2$), 3.60 (s, 3H, $OCH_3$), 3.34 (s, 3H, $NCH_3$).

Part E: Preparation of 4-N'-(2',2'-Diphenylimino)-N-methoxyl-N-methylcarboxamide A mixture of N'-Methoxyl-N'-methyl-4-aminobenzenecarboxamide (18 g, 0.10 mole), benzophenone imine (19 g, 0.11 mole), boron trifluoride etherate (5 mL) and toluene (400 mL) was stirred and heated to reflux under a nitrogen atmosphere for 4 hours. The mixture was cooled to ambient temperature and washed with saturated aqueous sodium bicarbonate (100 mL), water (100 mL) and brine (100 mL). The dried ($MgSO_4$) organic layer was evaporated in vacuo to leave a yellow solid that recrystallized from hexanes-EtOAc (23 g, 67%). The filtrate was condensed and chromatographed on silica gel eluting with a gradient of 25% hexane/EtOAc to 33% hexane/EtOAc to 50% hexane/EtOAc. Another 4.7 g (14%) of product was isolated. Total yield=27.7 g (81%). Mp 123°–6° C. 200 MHz $^1$H-NMR ($CDCl_3$); $\delta$7.53 (d, 2H, J=7.8 Hz, $H^2$), 7.40 (m, 10H, ArH), 6.72 (d, 2H, J=7.8 Hz, $H^3$), 3.50 (s, 3H, $OCH_3$), 3.30 (s, 3H, $NCH_3$).

Part F: Preparation of 2-(1,3-Dioxolan-2-yl)-4-diphenylimino-4,5-methylenedioxybenzophenone An oven dried, 3-necked, 250 mL flask was purged with nitrogen, charged with 5-bromo-6-(1,3-dioxolanyl-2-yl)-2,3-methylenedioxybenzene (7.5 g, 27 mmole) and THF (80 mL, freshly distilled from sodium benzophenone ketyl). The solution was cooled to –78° C. and n-butyl lithium (12 mL of a 2.5M solution in hexanes, 30 mmole) was added dropwise over 5 minutes. Two minutes after the addition of butyl lithium was completed the solution was added via cannula to a solution of 4-N'-(2',2'-Diphenylimino)-N-methoxyl-N-methylcarboxamide (9.5 g, 27 mmole) and distilled THF (80 mL) in an oven dried, nitrogen purged, 3-necked, 500 mL flask at -78° C. After 15 minutes the dry-ice bath was removed and the mixture stirred 14 hours at 20° C. and then was poured into a mixture of EtOAc (500 mL) and water (200 mL). The layers were separated, the aqueous layer was extracted with EtOAc (100 mL), combined with the earlier organic layer, dried ($MgSO_4$) and evaporated to leave a yellow solid. Recrystallization from EtOAc provided bright yellow needles (8.2 g, 64%). Mp 187°–9° C. 200 MHz $^1$H-NMR ($CDCl_3$); $\delta$7.68 (d, 2H, J=8.4 Hz), 7.40 (m, 10H, ArH), 6.76 (s, 1H), 6.75 (d, 2H, J=8.4 Hz), 6.06 (s, 2H, $OCH_2O$), 5.81 (s, 1H, OCHO), 3.85 (m, 4H, $OCH_2CH_2O$): FAB LRMS (mBNA); 478 (M+1).

Part G: Preparation of 1-(4-Aminophenyl)-6,7-methylendioxyphthalazine 2-(1,3-Dioxolan-2-yl)-4'-diphenylimino-4,5-methylenedioxy-benzo phenone (5.7 g, 12 mmole) and hydrazine dihydrochloride (1.4 g, 13 mmole) were dissolved in methanol (250 mL) and water (25 mL). Hydrazine (0.42 g, 13 mmole) was added and the mixture stirred for 16 hours at 20° C. The solvents were evaporated in vacuo to one quarter the original volume, EtOAc (300 mL), water (300 mL) and 1N HCl (10 mL) were added. The organic layer was further washed with water and the combined aqueous layers were neutralized with 1N NaOH. The precipitate was extracted with dichloromethane (4×500 mL), dried ($MgSO_4$) and evaporated to leave a tan solid. The crude product was chromatographed on silica gel eluting with 10% methanol/EtOAc to afford the aminophenylphthalazine as a tan solid (2.2 g, 69%). Mp 221°–223° C. (dec.). 200 MHz $^1$H-NMR ($CDCl_3$); $\delta$9.28 (s, 1H), 7.58 (d, 2H, J=8.6 Hz), 7.41 (s, 1H), 7.21 (s, 1H), 6.84 (d, 2H, J=8.6 Hz), 6.17 (s, 2H, OCHO), 3.90 (bs, 2H, $NH_2$): FAB LRMS (mNBA); 266 (M+1).

Part H: Preparation of 1-(4-Acetylaminophenyl)-6,7-methylendioxyphthalazine 1-(4-Aminophenyl)-6,7-methylendioxyphthalazine (3.0 g, 11 mmole) and acetic anhydride (50 mL) were stirred at ambient temperature for 3 h. The dark green mixture was cooled in an ice bath and treated with 1N HCl (200 mL). After 30 min the mixture was filtered through celite, neutralized with solid sodium carbonate and the resulting precipitate was filtered, washed with water (3×50 mL) and vacuum dried to leave a tan solid (3.1 g, 92%). A 0.17 g sample was recrystallized from methanol-water to leave a light yellow solid. TLC is homogeneous (20% methanol/EtOAc). Mp 268°–270° C. (dec.). 200 MHz $^1$H-NMR (DMSO-$d_6$); $\delta$10.30 (brs, 1H, NH), 9.53 (s, 1H), 7.93 (d, 2H, J=7.0 Hz), 7.76 (d, 2H, J=7.0 Hz), 7.75 (s, 1H), 7.37 (s, 1H), 6.43 (s, 2H, OCHO), 2.24 (s, 3H, $COCH_3$): CI ($CH_4$) LRMS; 308 (M+1).

Part I: Preparation of 4-(4-Acetylaminophenyl)-1,2-dihydro-1-methyl-6,7-methylenedioxyphthalazine An oven dried, 3-necked, 250 mL flask was purged with nitrogen and charged with 1-(4-acetylaminophenyl)-6,7-methylendioxyphthalazine (1.0 g, 3.3 mmole), distilled THF (30 mL) and TMEDA (10 mL). The suspension was cooled in an ice bath and treated dropwise over five minutes with an ether solution of methyl lithium (9.3 mL of a 1.4M solution, 13 mmole). The dark brown mixture was stirred for 1 h, treated cautiously with water (5 mL) then dichloromethane (120 mL). The contents of the flask were transferred to a separatory funnel, water (100 mL) was added and the layers were separated. The aqueous phase was further extracted with dichloromethane (50 mL), the extracts combined, washed with brine (100 mL), dried ($MgSO_4$) and evaporated in vacuo. The tan foamy residue was dissolved in methanol (20 mL), silica gel was added and the solvent was evaporated to complete dryness. The crude product was chromatographed on silica gel eluted with EtOAc to afford the addition product a light tan crystalline solid (0.53 g, 50%). Mp 236°–239° C. 200 MHz $^1$H-NMR ($CDCl_3$); $\delta$7.59 (s, 4H), 7.26 (brs, 1H, N$\underline{H}$COCH$_3$), 6.75 (s, 1H), 6.73 (s, 1H), 6.00 (s, 2H, OCHO), 5.88 (brs, 1H), 4.31 (q, 1H, J=6.4 Hz, —C$\underline{H}$CH$_3$), 2.60 (s, 3H, $COCH_3$), 1.48 (d, 3H, J=6.4 Hz, CHC$\underline{H}_3$).

Part J: Preparation of 4-(4-Acetylaminophenyl)-1,2-dihydro-1-methyl-2-(N"-methylcarbamoyl)-6,7-methylendioxyphthalazine To a suspension of 4-(4-acetylaminophenyl)-1,2-dihydro-1-methyl1-6,7-methylendioxy phthalazine (0.27 g, 1.2 mmole) in dichloromethane (20 mL) was added dimethylaminopyridine (DMAP, 20 mg) and a large excess of methylisocyanate (1.0 mL). The mixture stirred at ambient temperature for 24 h. during which time the phthalazine dissolved completely. More methylisocyanate (1 mL) was added, the solution stirred another 24 hours and the mixture was blown to near dryness with a stream of nitrogen. The residue was chromatographed on silica gel and eluted with 5% methanol/dichloromethane. The desired product was obtained as a light yellow powder (0.27 g, 81%). 200 MHz $^1$H-NMR (DMSO-d$_6$); δ7.83 (s, 4H'), 7.31 (q, 1H, J=5.7 Hz, NHCH$_3$), 7.25 (s, 1H), 6.85 (s, 1H), 6.23 (s, 1H, OCHO), 6.21 (s, 1H, OCHO), 5.90 (s, 1H, NHCOCH$_3$), 5.70 (q, 1H, J=7.1 Hz, CHCH$_3$), 2.88 (d, 3H, J=5.7 Hz, NHCH$_3$), 2.23 (s, 3H, COCH$_3$), 1.22 (d, 3H, J=7.1 Hz, CHCH$_3$): CI (CH$_4$) LRMS; 381 (M+1).

Part K: Preparation of 4-(4-Aminophenyl)-1,2-dihydro-1-methyl-2-(N"-methylcarbamoyl)-6,7-methylendioxyphthalazine A solution of 4-(4-acetylaminophenyl)-1,2-dihydro-1-methyl-2-(N"-methylcarbamoyl)-6,7-methylendioxyphthalazine (186 mg, 0.49 mmole), 1N NaOH (3 mL) and methanol (7 mL) was heated to reflux for 72 hours, cooled to ambient temperature and diluted with water (10 mL) and dichloromethane (20 mL). The aqueous phase was further extracted with dichloromethane (2×10 mL), combined with the earlier organic phase, dried (MgSO$_4$) and evaporated in vacuo to leave a yellow foamy residue. Chromatography on silica gel (25% hexanes/EtOAc) provided as a light yellow foamy solid (115 mg, 69%). 200 MHz $^1$H-NMR (DMSO-d$_6$); δ7.55 (d, 2H, J=8.8 Hz), 7.20 (s, 1H), 7.18 (q, 1H, J=4.4 Hz, NHCH$_3$), 6.87 (s, 1H), 6.76 (d, 2H, J=8.8 Hz), 6.21 (s, 1H, OCH$_2$O), 6.18 (s, 1H), 5.64 (q, 1H, J=7.3 Hz, CHCH$_3$), 5.56 (bs, 2H, NH$_2$), 2.86 (d, 3H, J=4.4 Hz, NHCH$_3$), 1.17 (d, 3H, J=7.3 Hz, CHCH$_3$): CI (CH$_4$) LRMS; 339 (M+1).

EXAMPLE 2

Preparation of 4-(4-Aminophenyl)-1,2-dihydro-2-(N-ethylcarbamoyl)-1-methyl-6,7-methylendioxyphthalazine Part A: Preparation of 4-(4-Acetylaminophenyl)-1,2-dihydro-2-(N-ethylcarbamoyl)-1-methyl-6,7-methylendioxyphthalazine A suspension of 4-(4-acetylaminophenyl)-1,2-dihydro-1-methyl-6,7-methylendioxyphthalazine (0.10 g, 0.31 mmole) in dichloromethane was treated with ethylisocyanate (1 mL). After stirring for 2 hours more ethylisocyanate (1 mL) was added and the mixture stirred an additional 14 hours Another portion of ethylisocyanate (1 mL) was added and the solution stirred another 6 h. A stream of nitrogen was blown through the reaction mixture until dryness. The residue was chromatographed on silica gel eluted with a gradient of 75% EtOAc/hexanes to 100% EtOAc. The product was obtained as a tan foamy residue (106 mg, 87%). 200 MHz $^1$H NMR (CDCl$_3$); δ7.60 (q, 4H, J=10.0 Hz, ArH), 7.32 (s, 1H, NHCOCH$_3$), 6.73 (s, 1H, ArH), 6.70 (s, 1H, ArH), 6.51 (t, 1H, J=5.0 Hz, CONHCH$_2$), 5.98 (s, 2H, OCH$_2$O), 5.68 (q, 1H, J=6.7 Hz, CHCH$_3$), 4.12 and 3.38 (m, 2H, NHCH$_2$CH$_3$), 2.23 (s, 3H, COCH$_3$), 1.34 and 1.20 (t, J=7.0 Hz and J=8.0 Hz, CH$_2$CHH$_3$), 1.23 (d, 3H, J=6.7 Hz, CHCH$_3$).

Part B: Preparation of 4-(4-Aminophenyl)-1,2-dihydro-2-(N-ethylcarbamoyl)-1-methyl-6,7-methylendioxyphthalazine To a solution of the above dihydrophthalazine (0.10 g, 0.26 mmole) in methanol (4 mL) was added 1N sodium hydroxide (2 mL). The mixture was stirred and heated to reflux for 72 hours. After cooling to ambient temperature the solution was diluted with EtOAc (25 mL), washed with water (50 mL), dried (MgSO$_4$) and evaporated in vacuo. The residue was chromatographed on silica gel eluted with a gradient of 50% EtOAc/hexanes to 67% EtOAc/hexanes to afford the product as a light yellow foamy solid (77 mg, 84%). 200 MHz $^1$H NMR (CDCl$_3$); δ7.45 (d, 2H, J=9.4 Hz, ArH$_2$'), 6.84 (s, 1H, ArH), 6.79 (d, 2H, J=9.4 Hz, ArH$_3$'), 6.73 (s, 1H, ArH), 6.57 (t, 1H, J=4.7 Hz, CONH), 6.02 (s, 2H, OCH$_2$O), 5.70 (q, 1H, J=7.8 Hz, CHCH$_3$), 3.90 (bs, 2H, NH$_2$), 3.41 (m, 2H, NHCH$_2$), 1.27 (d, 3H, J=7.8 Hz, CHCH$_3$), 1.20 (t, 3H, J=7.0 Hz, CH$_2$CH$_3$): CI LRMS (CH$_4$); 353 (M+1).

EXAMPLE 3

Preparation of 4-(4-Aminophenyl)-1,2-dihydro-1-methyl-2-propylcarbamoyl-6,7-methylendioxyphthalazine Part A: Preparation of 4-(4-Acetylaminophenyl)-1,2-dihydro-1-methyl-2-propylcarbamoyl -6,7-methylendioxyphthalazine A mixture of 4-(4-acetylaminophenyl)-1,2-dihydro-1-methyl-6,7-methylendioxyphthalazine (0.10 g, 0.31 mmole) and dichloromethane (5 mL) was stirred and treated with propylisocyanate (0.5 mL). After 5 hours more propylisocyanate (0.5 mL) was added and the mixture stirred for 48 h. The solvents were blown dry with a stream of nitrogen and the residue was chromatographed on silica gel eluted with a gradient of 33% hexanes/EtOAc to 25% hexanes/EtOAc. The resultant product was a light yellow foamy solid (108 mg, 86%). 200 MHz $^1$H NMR (CDCl$_3$); δ7.63 (ABq, 4H, J=9.4 Hz, ArH'), 7.40 (bs, 1H, ArNH), 6.77 (s, 1H, ArH), 6.74 (s, 1H, ArH), 6.62 (t, 1H, J=8.5 Hz, NHCH$_2$), 6.02 (s, 2H, OCH$_2$O), 5.71 (q, 1H, J=10.9 Hz, CHCH$_3$), 3.33 (dt, 1H, J=8.5 Hz, J=7.8 Hz, NHCHCH$_2$), 2.18 (s, 3H, COCH$_3$), 1.61 (q, 2H, J=7.8 Hz, CH$_2$CH$_2$CH$_3$), 1.27 (d, 3H, J=10.9 Hz, CHCH$_3$), 0.98 (t, 3H, J=7.8 Hz, CH$_2$CH$_3$).

Part B: Preparation of 4-(4-Aminophenyl)-1,2-dihydro-1-methyl-2-propylcarbamoyl-6,7-methylendioxyphthalazine A solution of the above dihydrophthalazine (0.10 g, 0.25 mmole) in 1N sodium hydroxide (4 mL) and methanol (8 mL) was stirred and heated to reflux for 72 hours. The solution was cooled to ambient temperature, diluted with EtOAc (30 mL) and washed with water (30 mL). The aqueous layer was extracted with EtOAc (25 mL) and the combined organic layers were dried (MgSO$_4$) and evaporated in vacuo. The crude product was chromatographed on silica gel eluted with 50% hexanes/EtOAc to afford the pure product as a light yellow foamy solid (75 mg, 82%). 200 MHz $^1$H NMR (CDCl$_3$); δ7.41 (d, 2H, J=6.5 Hz, ArH), 6.81 (s, 1H, ArH), 6.77 (d, 2H, J=6.5 Hz, ArH), 6.71 (s, 1H, ArH), 6.00 (s, 2H, OCH$_2$O), 5.67 (q, 1H, J=6.7 Hz, CHCH$_3$), 3.85 (brs, 2H, NH$_2$), 3.30 (dt, 2H, J=8.3 Hz, J=6.2 Hz, NHCH$_2$CH$_2$), 1.58 (m, 2H, CH$_2$CH$_2$CH$_3$), 1.24 (d, 3H, J=6.7 Hz, CHCH$_3$), 0.95 (t, 3H, J=7.5 Hz, CH$_2$CH$_3$).

EXAMPLE 4

Preparation of 4-(4-Aminophenyl)-1,2-dihydro-1-methyl-2-isopropylcarbamoyl-6,7-methylendioxyphthalazine Part A: Preparation of 4-(4-Acetylaminophenyl)-1,3-dihydro-2-methyl-3-isopropylcarbamoyl-6,7-methylendioxyphthalazine A mixture of 4-(4-acetylaminophenyl)-1,2-dihydro-1-methyl-6,7-methylendioxyphthalazine (0.10 g, 0.31 mmole) and dichloromethane (5 mL) were stirred and treated with isopropylisocyanate (0.5 mL). The mixture stirred for 5 hours and was treated again with isopropylisocyanate (0.5 mL). The mixture stirred another 14 hours at which point it was treated again with isopropylisocyanate (0.5 mL). After another 5 hours of stirring the solution was blown dry with a stream of nitrogen and the residue was chromatographed on silica gel (33% hexanes/EtOAc). The resultant product was a light yellow foamy solid (103 mg, 82%). 200 MHz $^1$H NMR (CDCl$_3$); $\delta$7.63 (ABq, 4H, J=12.5 Hz, ArH), 7.47 (brs, 1H, ArNH), 6.77 (s, 1H, ArH), 6.72 (s, 1H, ArH), 6.40 (d, 1H, J=10.0 Hz, N$\underline{H}$CH), 6.01 (s, 2H, OCH$_2$O), 5.71 (q, 1H, J=9.2 Hz, C$\underline{H}$CH$_3$), 4.07 and 3.90 (m, 1H, NHC$\underline{H}$), 2.27 (s, 3H, COCH$_3$), 1.25 (d, 3H, J=9.2 Hz, CHC$\underline{H}_3$), 1.23 and 1.17 (m, 6H, J=9.4 Hz, CH(C$\underline{H}_3$)$_2$).

Part B: Preparation of 4-(4-Aminophenyl)-1,2-dihydro-1-methyl-2-isopropylcarbamoyl-6,7-methylendioxyphthalazine A solution of the dihydrophthalazine Pan A in 1N sodium hydroxide (4 mL) and methanol (8 mL) was stirred and heated to reflux for 72 hours. The mixture was cooled to ambient temperature, diluted with EtOAc (30 mL) and washed with water (30 mL). The aqueous layer was extracted with EtOAc (20 mL) and the combined organic layers were dried (MgSO$_4$) and evaporated. The residue was chromatographed on silica gel eluted with 50% hexanes/EtOAc to leave the product as a light yellow solid (75 mg, 82%). 200 MHz $^1$H NMR (CDCl$_3$); $\delta$7.42 (d, 2H, J=6.5 Hz, ArH'), 6.80 (s, 1H, ArH), 6.77 (d, 2H, J=6.5 Hz, ArH), 6.71 (s, 1H, ArH), 6.39 (d, 1H, J=11.0 Hz, N$\underline{H}$CH), 5.99 (s, 2H, OCH$_2$O), 5.67 (q, 1H, J=6.2 Hz, C$\underline{H}$CH$_3$), 4.10 (m, 1H, C$\underline{H}$(CH$_3$)$_2$), 3.89 (brs, 2H, NH$_2$), 1.24 (d, 3H, J=6.2 Hz, CHC$\underline{H}_3$), 1.23 (d, 6H, J=6.6 Hz, CH(C$\underline{H}_3$)$_2$): FTIR (PTFE film); 3344 cm$^{-1}$, 2923, 2851, 1662, 1610, 1503, 1390, 1364, 1072, 1036.

EXAMPLE 11

Preparation of 4-(4-Aminophenyl)-1,2-dihydro-1-ethyl-2-methylcarbamoyl-6,7-methylendioxyphthalazine Part A: Preparation of 4-(4-acetylaminophenyl)-1,2-dihydro-1-ethyl-6,7-methylendioxyphthalazine An oven dried, 3-necked, 50 mL flask was purged with nitrogen and charged with the 1-(4-aminophenyl)-6,7-methylendioxyphthalazine (0.20 g, 0.65 mmole) and THF (distilled from sodium benzophenone ketyl). The mixture was cooled in an ice bath and treated with ethyl magnesium bromide in ether (0.54 mL of a 3.0M solution, 1.6 mmole). The ice bath was removed and the mixture stirred for 14 h. It was recooled in an ice bath, treated with 1N HCl (25 mL) and dichloromethane (20 mL). The aqueous layer was separated and neutralized with solid sodium carbonate (pH= 12). The product was extracted with dichloromethane (3×25 mL). All organic phases were combined, dried (MgSO$_4$) and evaporated. The residue was chromatographed on silica gel eluted with EtOAc to afford the product as a light yellow foamy solid (68 mg, 31%). 200 MHz $^1$H NMR (CDCl$_3$); $\delta$7.57 (s, 4H, ArH), 7.23 (bs, 1H, ArNH), 6.75 (s, 1H, ArH), 6.68 (s, 1H, ArH), 5.59 (s, 2H, OCH$_2$O), 4.02 (t, 1H, J=6.9 Hz, C$\underline{H}$CH$_2$), 2.23 (s, 3H, COCH$_3$), 1.75 (m, 2H, CHC$\underline{H}_2$CH$_3$), 1.02 (t, 3H, J=7.6 Hz, CH$_2$CH$_3$).

Part B: Preparation of 4-(4-Acetylaminophenyl)-1,2-dihydro-1-ethyl-2-methylcarbamoyl-6,7-methylendioxyphthalazine A solution of 4-(4-acetylaminophenyl)-1,2-dihydro-1-ethyl-6,7-methylendioxyphthalazine (60 mg, 0.18 mmole) and THF (6 mL) were stirred and treated with methylisocyanate (0.25 mL). The mixture was heated to reflux for 5 hours and more methylisocyanate (0.25 mL) was added. Reflux continued for another 14 hours and the mixture was then blown dry with a stream of nitrogen. The residue was chromatographed on silica gel with 5% methanol/dichloromethane to leave the product as a light yellow foamy solid (52 mg, 73%). 200 MHz $^1$H NMR (CDCl$_3$); $\delta$7.59 (q, 4H, J=5.1 Hz, ArH), 7.28 (bs, 1H, ArNH), 6.74 (s, 1H, ArH), 6.69 (s, 1H, ArH), 6.48 (q, 1H, J=4.8 Hz, N$\underline{H}$CH$_3$), 5.99 (d, 2H, J=2.2 Hz, OCH$_2$O), 5.50 (t, 1H, J=6.2 Hz, C$\underline{H}$CH$_2$), 2.93 and 2.86 (d pair, 3H, J=5.0 Hz and J=4.6 Hz, NHC$\underline{H}_3$), 2.23 and 2.17 (s pair, 3H, COCH$_3$), 1.65 (m, 2H, CHC$\underline{H}_2$CH$_3$), 0.87 (t, 3H, J=8.3 Hz, CH$_2$C$\underline{H}_3$).

Part C: Preparation of 4-(4-Aminophenyl)-1,2-dihydro-1-ethyl-2-methylcarbamoyl-6,7-methylendioxyphthalazine A solution of 4-(4-acetylaminophenyl)-1,2-dihydro-1-ethyl-2-methylcarbamoyl-6,7-methylendioxyphthalazine (45 mg, 0.11 mmole) in 1N sodium hydroxide (4 mL) and methanol (6 mL) was heated to reflux for 72 hours. The mixture was cooled to ambient temperature, diluted with EtOAc (30 mL), washed with water (25 mL), dried (MgSO$_4$) and evaporated in vacuo. The residue was chromatographed on silica gel with 25% hexanes/EtOAc to afford the product as a light yellow foamy solid (35 mg, 90%). 200 MHz $^1$H NMR (CDCl$_3$); $\delta$7.42 (d, 2H, J=8.1 Hz, ArH), 6.82 (s, 1H, ArH), 6.76 (d, 2H, J=8.1 Hz, ArH), 6.70 (s, 1H, ArH), 6.50 (brq, 1H, J=5.4 Hz, N$\underline{H}$CH$_3$), 5.59 (d, 2H, J=2.7 Hz, OCH$_2$O), 5.48 (t, 1H, J=6.8 Hz, C$\underline{H}$CH$_2$), 2.93 (d, 3H, J=5.4 Hz, NHC$\underline{H}_3$), 1.64 (m, 2H, CHC$\underline{H}_2$CH$_3$), 0.87 (t, 3H, J=8.1 Hz, CH$_2$C$\underline{H}_3$).

EXAMPLE 23

Preparation of 4-(4-Aminophenyl)-1,2-dihydro-2-methoxycarbonyl-6,7-methylendioxyphthalazine Part A: Preparation of 4-(4-Acetylaminophenyl)-1,2-dihydro-2-methoxycarbonyl-1-methyl-6,7-methylendioxyphthalazine To a suspension of 4-(4-acetylaminophenyl)-1,2-dihydro-1-methyl-6,7-methylendioxyphthalazine (0.10g, 0.31 mmole) in THF (5 mL, freshly distilled from sodium benzophenone ketyl) and triethylamine (63 mg, 0.62 mmole, 86 mL) was added methylchloroformate (1 mL) over 1 minute with rapid stirring. After 2 hours more methylchloroformate was added (1 mL) and the mixture was allowed to stir an additional hour. The solvents were evaporated in vacuo and the residue was diluted with water (15 mL) and EtOAc (25 mL). The organic phase was separated, dried (MgSO$_4$) and evaporated. The residue was chromatographed on silica gel eluted with a gradient of 80% EtOAc/hexanes to 100% EtOAc. The product was obtained as a light yellow foamy solid (125 mg, 98%). 200 MHz $^1$H NMR (CDCl$_3$); $\delta$7.63 (s, 4H, ArH), 7.38 (bs, 1H, NH), 6.77 (s, 1H, ArH), 6.70 (s, 1H, ArH), 6.00 (s, 2H, OCH$_2$O), 5.52 (q, 1H, J=6.2 Hz, C$\underline{H}$CH$_3$), 3.90 (s, 3H, OCH$_3$), 2.21 (s, 3H, COCH$_3$), 1.31 (d, 3H, J=6.2 Hz, CHC$\underline{H}_3$).

Part B: Preparation of 4-(4-Aminophenyl)-1,2-dihydro-2-methoxycarbonyl-1-methyl-6,7-methylendioxyphthalazine To a solution of the above dihydrophthalazine (83 mg, 0.22 mmole), 4-dimethyl-aminopyridine (27 mg, 0.22 mmole), triethylamine (22 mg, 0.22 mmole) and dichloromethane (4 mL) was added t-butyloxycarbonyl anhydride (95 mg, 0.44 mmole). The mixture was stirred for 6 hours, diluted with dichloromethane (25 mL), washed with 10% citric acid, dried (MgSO$_4$) and evaporated in vacuo. The residue was dissolved in THF (5 mL) and water (5 mL), treated with lithium hydroxide monohydrate and stirred for 2 hours. The solution was diluted with brine (15 mL) and dichloromethane (40 mL), the aqueous layer was washed with dichloromethane, the organic layers were combined, dried (MgSO$_4$) and evaporated in vacuo. The residue was treated with dichloromethane (4 mL) and TFA (4 mL), stirred for 30 minutes, evaporated, treated with toluene, evaporated and the residue was dissolved in 1N sodium hydroxide (10 mL) and EtOAc (10 mL). The organic layer was separated, dried (MgSO$_4$) and evaporated. The residue was chromatographed on silica gel eluted with a gradient of 50% EtOAc/hexanes to 75% EtOAc/hexanes. The product was obtained as a light yellow foamy solid (37 mg, 64%). 200 MHz $^1$H NMR (CDCl$_3$); δ7.47 (d, 2H, J=8.3 Hz, ArH), 6.83 (s, 1H, ArH), 6.73 (d, 2H, J=8.3 Hz, ArH), 6.69 (s, 1H, ArH), 5.59 (s, 2H, OCH$_2$O), 5.50 (q, 1H, J=6.7 Hz, CHCH$_3$), 3.88 (s, 3H, OCH$_3$), 3.84 (bs, 2H, NH$_2$), 1.30 (d, 3H, J=6.7 Hz, CHCH$_3$): CI LRMS (CH$_4$); 340 (M+1).

EXAMPLE 31

Preparation of 4-(4-Aminophenyl)-1,2-dihydro-2-(N,N-dimethylcarbamoyl)-1-methyl-6,7-methylendioxyphthalazine Part A: Preparation of 4-(4-Acetylaminophenyl)-1,2-dihydro-2-(N,N-dimethylcarbamoyl)-1-methyl-6,7-methylendioxyphthalazine A solution of 4-(4-acetylaminophenyl)-1,2-dihydro-1-methyl-6,7-methylendioxyphthalazine (0.10 g, 0.31 mmole), 4-dimethylaminopyridine (20 mg) and diisopropylethylamine (0.50 mL) in THF was treated with N,N-dimethylcarbamoyl chloride (0.50 mL). The mixture was heated to reflux for 14 hours, cooled to ambient temperature, diluted with dichloromethane (20 mL), washed with 0.2N HCl (20 mL), dried (MgSO$_4$) and evaporated in vacuo to leave a green solid that was chromatographed on silica gel with EtOAc. The pure product was a beige solid (107 mg, 88%). 200 MHz $^1$H NMR (CDCl$_3$); δ7.62 (s, 4H, ArH), 6.77 (s, 1H, ArH), 6.70 (s, 1H, ArH), 6.00 (d, 2H, J=2.1 Hz, OCH$_2$O), 5.27 (q, 1H, J=6.2 Hz, CHCH$_3$), 3.06 (s, 6H, N(CH$_3$)$_2$), 2.23 (s, 3H, COCH$_3$), 1.32 (d, 3H, J=6.2 Hz, CHCH$_3$).

Part B: Preparation of 4-(4-Aminophenyl)-1,2-dihydro-2-(N,N-dimethylcarbamoyl)-1-methyl-6,7-methylendioxyphthalazine A solution of 4-(4-acetylaminophenyl)-1,2-dihydro-2-(N,N-dimethylcarbamoyl)-1-methyl-6,7-methylendioxyphthalazine (97 mg, 0.25 mmole) in 1N sodium hydroxide (3 mL) and methanol (7 mL) was heated to reflux for 72 hours, cooled to ambient temperature, diluted with EtOAc (25 mL) and water (25 mL). The aqueous layer was washed with EtOAc and the combined organic layers were dried (MgSO$_4$) and evaporated. The residue was chromatographed on silica gel with 25% hexanes/EtOAc to leave a light yellow foamy solid (63 mg, 72%). 200 MHz $^1$H NMR (CDCl$_3$); δ7.45 (d, 2H, J=8.6 Hz, ArH$_2$'), 6.84 (s, 1H, ArH), 6.76 (d, 2H, J=8.6 Hz, ArH), 6.71 (s, 1H, ArH), 6.01 (d, 2H, J=2.9 Hz, OCH$_2$O), 5.25 (q, 1H, J=7.1 Hz, CHCH$_3$), 3.95 (brs, 2H, NH$_2$), 3.07 (s, 6H, N(CH$_3$)$_2$), 1.33 (d, 3H, J=7.1 Hz, CHCH$_3$): FTIR (PTFE film); 3456 cm$^{-1}$, 3343, 3220, 1631, 1605, 1482, 1379, 1251, 1036.

EXAMPLE 185

Synthesis of 4-(4-Aminophenyl)-1-methyl-6,7-methylenedioxyphthalazine

Part A: 4-(4-Acetylaminophenyl)-1,2-dihydro-1-methyl-6,7-methylenedioxyphthalazine An oven dried, 3-necked, 250 mL flask was purged with nitrogen and charged with 1-(4-acetylaminophenyl)-6,7-methylendioxyphthalazine (1.0 g, 3.3 mmole), distilled THF (30 mL) and TMEDA (10 mL). The suspension was cooled in an ice bath and treated dropwise over five minutes with an ether solution of methyl lithium (9.3 mL of a 1.4M solution, 13 mmole). The dark brown mixture was stirred for 1 h, treated cautiously with water (5 mL) then dichloromethane (120 mL). The contents of the flask were transferred to a separatory funnel, water (100 mL) was added and the layers were separated. The aqueous phase was further extracted with dichloromethane (50 mL), the extracts combined, washed with brine (100 mL), dried (MgSO$_4$) and evaporated in vacuo. The tan foamy residue was dissolved in methanol (20 mL), silica gel was added and the solvent was evaporated to complete dryness. The crude product was chromatographed on silica gel eluted with EtOAc to afford the addition product a light tan crystalline solid (0.53 g, 50%). Mp 236°–239° C. 200 MHz $^1$H-NMR (CDCl$_3$); δ7.59 (s, 4H), 7.26 (brs, 1H, NHCOCH$_3$), 6.75 (s, 1H), 6.73 (s, 1H), 6.00 (s, 2H, OCHO), 5.88 (brs, 1H), 4.31 (q, 1H, J=6.4 Hz, —CHCH$_3$), 2.60 (s, 3H, COCH$_3$), 1.48 (d, 3H, J=6.4 Hz, CHCH$_3$).

Part B: 4-(4-Aminophenyl)-1-methyl-6,7-methylenedioxy-1,2-dihydrophthalazine 4-(4-Aminophenyl)-6,7-methylenedioxyphthalazine (600 mg, 2.3 mmol) was suspensed in THF (25 mL) at 20° C. in an oven dried 3-necked flask under N$_2$. CH$_3$Li (6.5 mL, 9.1 mmol) in ether was added slowly and stirred for 30 min. The reaction was quenched by the addition of 1N HCl (50 mL) and then extracted with EtOAc (30 mL). The organic layer was extracted again with 1N HCl (100 mL) and then the combined aqueous layers neutralized with 1N NaOH. The aqueous mixture was then extracted with CH$_2$Cl$_2$ (3×50 mL) and the organic layers combined, dried with K$_2$CO$_3$ and evaporated to give a brown gum. The brown gum was chromatographed on silica-gel 4:1 EtOAc/hexane to give a yellow gum (320 mg, 50%). 200 MHz $^1$H-NMR (CDCl$_3$); δ7.64 (d, 2H), 7.35 (d, 2H), 6.56 (d, 2H), 6.06 (s, 2H), 4.29 (q, CH), 1.33 (d, CH$_3$).

Part C. 4-(4-Aminophenyl)-1-methyl-6,7-methylenedioxyphthalazine 4-(4-Aminophenyl)-1-methyl-6,7-methylenedioxyphthalazine (200 mg, 0.71 mmol) and Pd/C (25 mg) were suspended in toluene (15 mL) and heated to reflux under N$_2$ for 10 h. Upon cooling to 20° C. a beige solid appeared and was collected by filtration. Silica gel chromatography (9:1 EtOAc/MeOH) gave a yellow solid, 130 mg, (66%). 200 MHz $^1$H-NMR (CDCl$_3$); δ7.50 (d, 2H), 7.36 (d, 2H), 6.83 (d, 2H), 6.16 (s, CH$_2$) 2.93 (s, CH$_3$).

Modifications and variations of the present invention will be obvious to those skilled in the art from the foregoing detailed description. Such modifications and variations are intended to come within the scope of appended claims.

What is claimed is:

1. A compound of Formula I:
   wherein
   $R^1$, $R^3$ and $R^4$ are independently
   a) H,
   b) HO,
   c) $R^{11}$O—,
   d) halogen,
   e) C1–C3-alkyl,
   f) CF$_3$,
   g) $R^{12}$CO$_2$—, or
   h) R$_{12}$C(O)NH—,
   with the proviso that no more than two of $R^1$–$R^4$ can be iodo and that R1–R4 cannot be mixtures of b) and c);

$R^1$ and $R^2$, or $R^2$ and $R^3$, or $R^3$ and $R^4$ can be taken together to be
  a) —OCH$_2$O—, or
  b) —OCH$_2$CH$_2$O—;

$R^5$ and $R^6$ are independently
  a) H,
  b) C1–C6-alkyl,
  c) C3–C6-alkenyl,
  d) C3–C6 alkynyl,
  e) C3–C6-cycloalkyl,
  f) phenyl or substituted phenyl, where the phenyl is substituted with one or two substituents selected from the group consisting of C1–C3-alkyl, halogen, $R^{12}$HN—, $R^{12}$O—, CF$_3$—, $R^{11}$SO$_2$— and CO$_2R^{12}$, or
  g) phenyl-C1–C3-alkyl or substituted phenyl-C1–C3-alkyl, where the phenyl is substituted with one or two substituents selected from the group consisting of C1–C3-alkyl, halogen, $R^{12}$HN—, $R^{12}$O—, CF$_3$—, $R^{11}$SO$_2$— and CO$_2R^{12}$, with the proviso that $R^5$ and $R^6$ cannot both be phenyl or substituted phenyl;

$R^7$ is
  a) $R^{13}R^{14}$NC(O)—,
  b) $R^{13}R^{14}$NC(S)—,
  c) $R^{13}R^{14}$NC(NR$^{12}$)—,
  d) $R^{15}$OC(O)—,
  e) $R^{13}$C(O)—,
  f) $R^{13}R^{14}$NCH$_2$C(O)—,
  g) $R^{12}$O$_2$C—(CH$_2$)$_n$—,
  h) $R^{13}R^{14}$NC(O)—(CH$_2$)$_n$—,
  i) NC—(CH$_2$)$_n$—,
  j) C3–C6-alkenyl, or
  k) C3–C6-alkynyl $R^8$ and $R^9$ are independently
  a) H,
  b) $R^{13}R^{14}$N—,
  c) $R^3$NHC(NH)—,
  d) $R^2$HNC(O)—, or
  e) $R^2$C(O)NH—;

$R^{10}$ is
  a) H,
  b) C1–C3-alkyl,
  c) halogen,
  d) $R^{12}$HN—,
  e) $R^{12}$O—,
  f) CF$_3$—, or
  g) CO$_2R^{12}$;

$R^{11}$ is C1–C3-alkyl;

$R^{12}$ is H or C1–C3-alkyl;

$R^{13}$ and $R^{14}$ are independently
  a) H,
  b) C1–C10-alkyl,
  c) C1–C6-perfluoroalkyl,
  d) C3–C10-alkenyl,
  e) C3–C10-alkynyl, or
  f) C3–C6-cycloalkyl;

$R^{13}$ and $R^{14}$ taken together can be C3–C6-cycloalkyl that includes the nitrogen to which $R^{13}$ and $R^{14}$ are attached;

$R^{15}$ is C1–C6-alkyl, C3–C6-alkenyl, or C3–C6-cycloalkyl;

n is 1 to 6;

m is 0 to 2; and pharmaceutically acceptable salts thereof;

wherein $R^8$ and $R^9$ both are not H.

2. The compound of claim 1 of Formula I wherein
  $R^1$, $R_2$, $R^3$ and $R^4$ are independently H, $R^{11}$O—, halogen, or C1–C3-alkyl;
  $R^2$ and $R^3$ taken together can be —OCH$_2$O—;
  $R^7$ is
    a) $R^{13}R^{14}$NC(O)—,
    b) $R^{13}R^{14}$NC(NR$^{12}$)—,
    c) $R^{15}$OC(O)—,
    d) $R^{13}$C(O)—, or
    e) $R^{13}R^{14}$NC(S)—,
  $R^8$ and $R^9$ are independently H, H$_2$N—, or CH$_3$C(O)NH—; and
  pharmaceutically acceptable salts thereof;
  wherein $R^8$ and $R^9$ both are not H.

3. The compound of claim 2 of Formula 1 selected from the group consisting of
  4-(4-aminophenyl)-1,2-dihydro-1-methyl-2-ethylcarbamoyl-6,7-methylenedioxyphthalazine,
  4-(4-aminophenyl)-1,2-dihydro-1-methyl-2-propylcarbamoyl-6,7-methylenedioxy phthalazine,
  4-(4-aminophenyl)-1,2-dihydro-1-methyl-2-n-butylcarbamoyl-6,7-methylenedioxyphthalazine,
  4-(3-aminophenyl)-1,2-dihydro-1-methyl-2-n-butylcarbamoyl-6,7-methylenedioxyphthalazine,
  4-(4-aminophenyl)-1,2-dihydro-1-methyl-2-propylthiocarbamoyl-6,7-methylenedioxyphthalazine, and
  4-(4-acetylaminophenyl)-1,2-dihydro-1-methyl-6,7-methylenedioxyphthalazine.

4. A composition comprising a pharmaceutically acceptable carrier and a therapeutically effective amount for treating a disorder associated with excessive activation of the α-amino-3-hydroxy-5-methyl-4-isooxazoleproprionic acid (AMPA) subtype of the ionotropic excitatory amino acid (EAA) receptors of a compound of Formula I:

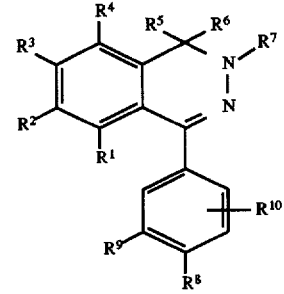

wherein
  $R^1$, $R^2$, $R^3$ and $R^4$ are independently
    a) H,
    b) HO,
    c) $R^{11}$O—,
    d) halogen,
    e) C1–C3-alkyl,
    f) CF$_3$,
    g) $R^{12}$CO$_2$—, or
    h) $R^{12}$C(O)NH—,
  with the proviso that no more than two of $R^1$–$R^4$ can be iodo and that R1–R4 cannot be mixtures of b) and c);
  $R^1$ and $R^2$, or $R^2$ and $R^3$, or $R^3$ and $R^4$ can be taken together to be
    a) —OCH$_2$O—, or
    b) —OCH$_2$CH$_2$O—;
  $R^5$ and $R^6$ are independently a) H,
b) C1–C6-alkyl,
c) C3–C6-alkenyl,
d) C3–C6 alkynyl,
e) C3–C6-cycloalkyl,
f) phenyl or substituted phenyl, where the phenyl is substituted with one or two substituents selected from the group consisting of C1–C3-alkyl, halogen, $R^{12}HN-$, $R^{12}O-$, $CF_3-$, $R^{11}SO_2-$ and $CO_2R^{12}$, or
g) phenyl-C1–C3-alkyl or substituted phenyl-C1–C3-alkyl, where the phenyl is substituted with one or two substituents selected from the group consisting of C1–C3-alkyl, halogen, $R^{12}HN-$, $R^{12}O-$, $CF_3-$, $R^{11}SO_2-$ and $CO_2R^{12}$, with the proviso that $R^5$ and $R^6$ cannot both be phenyl or substituted phenyl;

$R^7$ is
a) $R^{13}R^{14}NC(O)-$,
b) $R^{13}R^{14}NC(S)-$,
c) $R^{13}R^{14}NC(NR^2)-$,
d) $R^{15}OC(O)-$,
e) $R^{13}C(O)-$,
f) $R^{13}R^{14}NCH_2C(O)-$,
g) $R^{12}O_2C-(CH_2)_n-$,
h) $R^{13}R^{14}NC(O)-(CH_2)_n-$,
i) $NC-(CH_2)_n-$,
j) C3–C6-alkenyl, or
k) C3–C6-alkynyl $R^8$ and $R^9$ are independently
a) H,
b) $R^{13}R^{14}N-$,
c) $R^3NHC(NH)-$,
d) $R^{12}HNC(O)-$, or
e) $R_{12}C(O)NH-$;

$R^{10}$ is
a) H,
b) C1–C3-alkyl,
c) halogen,
d) $R^{12}HN-$,
e) $R^{12}O-$,
f) $CF_3-$, or
g) $CO_2R^{12}$;

$R^{11}$ is C1–C3-alkyl;
$R^{12}$ is H or C1–C3-alkyl;
$R^{13}$ and $R^{14}$ are independently
a) H,
b) C1–C10-alkyl,
c) C1–C6-perfluoroalkyl,
d) C3–C10-alkenyl,
e) C3–C10-alkynyl, or
f) C3–C6-cycloalkyl;

$R^{13}$ and $R^{14}$ taken together can be C3–C6-cycloalkyl that includes the nitrogen to which $R^{13}$ and $R^{14}$ are attached;

$R^{15}$ is C1–C6-alkyl, C3–C6-alkenyl, or C3–C6-cycloalkyl;
n is 1 to 6;
m is 0 to 2; and
pharmaceutically acceptable salts thereof;
wherein $R^8$ and $R^9$ both are not H.

5. A composition comprising a therapeutically effective amount of the compound of claim 2 for treating a disorder associated with excessive activation of the α-amino-3-hydroxy-5-methyl-4-isooxazoleproprionic acid (AMPA) subtype of the ionotropic excitatory amino acid (EAA) receptors and a pharmaceutically acceptable carrier.

6. A composition comprising a therapeutically effective amount of the compound of claim 3 for treating a disorder associated with excessive activation of the α-amino-3-hydroxy-5-methyl-4-isooxazoleproprionic acid (AMPA) subtype of the ionotropic excitatory amino acid (EAA) receptors and a pharmaceutically acceptable earlier.

7. A compound of Formula II:

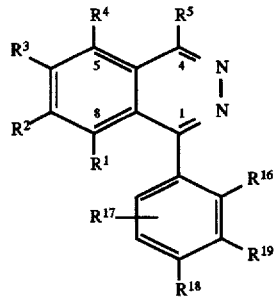

wherein
$R^1$, $R^2$, $R^3$ and $R^4$ are independently
a) H,
b) HO,
c) $R^{11}O-$,
d) halogen
e) C1–C3-alkyl,
f) $CF_3$,
g) $R^2CO_2-$, or
h) $R^{12}C(O)NH-$;

$R^1$ and $R^2$, or $R^2$ and $R^3$, or $R^3$ and $R^4$ can be taken together to be
a) $-OCH_2O-$, or
b) $-OCH_2CH_2O-$;

$R^5$ is
a) H,
b) C1–C6-alkyl,
c) C3–C6-alkenyl,
d) C3–C6-alkynyl,
e) C3–C6-cycloalkyl,
f) phenyl or substituted phenyl, wherein the phenyl is substituted with one or two substituents selected from the group consisting of C1–C3-alkyl, halogen, $R^{12}HN-$, $R^{12}O-$, $CF_3-$, $R^{11}SO_2-$ and $CO_2R^{12}$, or
g) phenyl-C1–C3-alkyl or substituted phenyl-C1–C3-alkyl, wherein the phenyl is substituted with one or two substituents selected from the group consisting of C1–C3-alkyl, halogen, $R^{12}HN-$, $R^{12}O-$, $CF_3-$, $R^{11}SO_2-$ and $CO_2R^{12}$;

$R^{11}$ is C1–C3-alkyl;
$R^{12}$ is H or C1–C3-alkyl;
$R^{16}$ and $R^{17}$ are independently
a) H,
b) C1–C3-alkyl,
c) halogen,
d) $R^{12}O-$,
e) $CF_3-$, or
f) $-CO_2R^{12}$;

$R^{18}$ and $R^{19}$ are independently
a) H,
b) $R^{13}R^{14}N-$,
c) $R^{13}NHC(NH)$, or
d) $R^{12}CONH-$;

and pharmaceutically acceptable salts thereof,
with the proviso that $R^{18}$ and $R^{19}$ cannot both be H.

8. The compound of claim 7 of Formula II wherein
R$^1$, R$^2$, R$^3$ and R$^4$ are independently H, R$^{11}$O—, halogen, or C1–C3-alkyl;
R$^2$ and R$^3$ taken together can be —OCH$_2$O—; and
R$^{18}$ and R$^{19}$ are independently H, NH$_2$ or CH$_3$C(O)NH—;
and pharmaceutically acceptable salts thereof.

9. The compound of claim 7 of Formula II selected from the group consisting of 1-(3-aminophenyl)-6,7-methylenedioxyphthalazine,
1-(3-amino-4-methylphenyl)-6,7-methylenedioxyphthalazine,
1-(3-amino-4-chlorophenyl)-6,7-methylenedioxyphthalazine,
1-(3-aminophenyl)-6-methoxyphthalazine,
1-(3-amino-4-methyl-phenyl)-6-methoxyphthalazine,
1-(3-amino-4-chloro-phenyl)-6-methoxyphthalazine
1-(4-aminophenyl)-6,7-methylenedioxyphthalazine,
1-(4-acetylaminophenyl)-6,7-methylenedioxyphthalazine,
4-(4-aminophenyl)-1-methyl-6,7-methylenedioxyphthalazine,
4-(4-acetylaminophenyl)-1-methyl-6,7-methylenedioxyphthalazine,
1-(4-aminophenyl)-7-methoxyphthalazine,
1-(4-acetylaminophenyl)-7-methoxyphthalazine,
4-(4-aminophenyl)-1-methyl-7-methoxyphthalazine, and
4-(4-acetylaminophenyl)-1-methyl-7-methoxyphthalazine.

* * * * *